United States Patent
Paget et al.

(10) Patent No.: US 6,770,664 B2
(45) Date of Patent: Aug. 3, 2004

(54) BICYCLIC HETEROCYCLIC SUBSTITUTED PHENYL OXAZOLIDINONE ANTIBACTERIALS, AND RELATED COMPOSITIONS AND METHODS

(76) Inventors: Steven D. Paget, 2 Camden Rd., Hillsborough, NJ (US) 08844; Dennis J. Hlasta, 5008 Davis Dr., Doylestown, PA (US) 18901

( * ) Notice: Subject to any disclaimer, the term of this patent is extended or adjusted under 35 U.S.C. 154(b) by 18 days.

(21) Appl. No.: 10/457,271

(22) Filed: Jun. 9, 2003

(65) Prior Publication Data

US 2004/0067994 A1 Apr. 8, 2004

Related U.S. Application Data

(63) Continuation of application No. 10/058,841, filed on Jan. 28, 2002, now Pat. No. 6,608,081, which is a continuation-in-part of application No. 09/621,814, filed on Jul. 21, 2000, now Pat. No. 6,413,981.
(60) Provisional application No. 06/148,621, filed on Jul. 12, 1999.

(51) Int. Cl.$^7$ ...................... A61K 31/42; A61K 31/415; C07D 263/02; C07D 413/00; C07D 231/00
(52) U.S. Cl. ...................... 514/374; 514/376; 514/377; 514/403; 514/405; 514/410; 514/412; 548/215; 548/225; 548/356.1; 548/360.1; 548/360.5; 548/364.1; 548/452; 548/453
(58) Field of Search ................. 514/374, 376, 514/377, 403, 405, 410, 412; 548/215, 225, 356.1, 360.1, 360.5, 364.1, 452, 453

(56) References Cited

U.S. PATENT DOCUMENTS

| | | |
|---|---|---|
| 3,391,150 A | 7/1968 | Weinstock |
| 5,037,834 A | 8/1991 | Brighty et al. |
| 5,312,823 A | 5/1994 | Petersen et al. |
| 5,371,090 A | 12/1994 | Petersen et al. |
| 5,565,571 A | 10/1996 | Barbachyn et al. |
| 5,654,428 A | 8/1997 | Barbachyn et al. |
| 5,792,765 A | 8/1998 | Riedl et al. |
| 5,827,857 A | 10/1998 | Riedl et al. |
| 5,837,870 A | 11/1998 | Pearlman et al. |
| 5,883,093 A | 3/1999 | Hutchinson et al. |
| 5,910,504 A | 6/1999 | Hutchinson |
| 5,929,248 A | 7/1999 | Barbachyn et al. |
| 6,090,820 A | 7/2000 | Barbachyn et al. |
| 6,124,334 A | 9/2000 | Hutchinson |
| 6,413,981 B1 | 7/2002 | Paget et al. |
| 6,608,081 B2 | 8/2003 | Paget et al. |

FOREIGN PATENT DOCUMENTS

| | | |
|---|---|---|
| EP | 0520277 A2 | 6/1992 |
| EP | 0539204 B1 | 4/1993 |
| JP | 11-322729 A | 11/1999 |
| WO | WO 93/09103 A1 | 5/1993 |
| WO | WO 93/13502 A1 | 7/1993 |
| WO | WO 95/07271 A1 | 3/1995 |
| WO | WO 96/13502 A1 | 5/1996 |
| WO | WO 96/15130 A1 | 5/1996 |
| WO | WO 96/23788 A1 | 8/1996 |
| WO | 9635691 | * 11/1996 |
| WO | WO 96/35691 A1 | 11/1996 |
| WO | WO 98/54161 A1 | 12/1998 |
| WO | WO 99/10342 A1 | 3/1999 |
| WO | WO 99/64416 A2 | 12/1999 |
| WO | WO 01/42242 A1 | 6/2001 |

OTHER PUBLICATIONS

Gawley, R.E. et al.; "(R,R)–1,3–Dibenzylisoindoline: A New C$_2$ Symmetric Secondary Amine, by Stereoselective and Regioselective a,a–Dialkylation of Isoindoline, and an Improved Procedure for the Preparation of Isoindoline", J. Org. Chem., 1988, 53:5381–5383.

(List continued on next page.)

Primary Examiner—Mukund J. Shah
Assistant Examiner—Sudhaker B. Patel

(57) ABSTRACT

Bicyclic heterocyclic substituted phenyl oxazolidinone compounds of the formula:

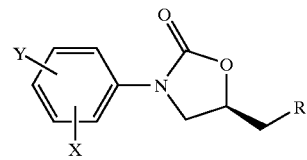

wherein Y is a radical of Formulae II or III:

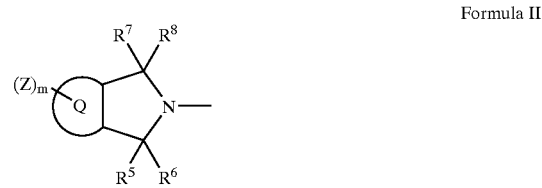

Formula II

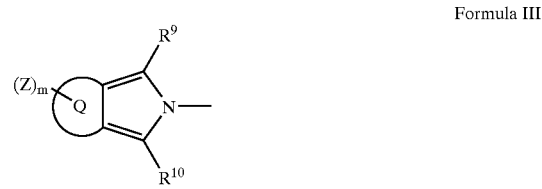

Formula III in which the substituents have the meaning indicated in the description. These compounds are useful as antibacterial agents.

5 Claims, No Drawings

OTHER PUBLICATIONS

Lewis, S.N. et al.; "Isothiazoles IV: 4–Isothiazolin–3–one 1–Oxide and 1,1–Dioxides", J. Heterocyclic Chem 1971, 8, 590–595.

Iwai, Issei et al.; "Studies on Acetylenic Compounds. XLIV. Synthesis of 3–Aminoisxazoles and 3–Hydroxyisoxazoles (3–Isoxazolones).", Chem Pharm Bull 1966, 14 (11), 1277–1286.

Brickner, S.J.; "Oxazolidinone Antibacterial Agents", Current Pharm. Design, 1996, vol. 2, No. 2, pp. 175–194.

Database WPI, Section Ch. Week 200006, Derwent Publications Ltd., London, GB; Class B03, AN 2000–069004, XP002154332 & JP 11 322729A (Hokuriku Pharm Co Ltd) Nov. 24, 1999 : Refer to Patent No. JP 11–322729–A enclosed herein.

International Search Report Application PCT/US 00/21093 dated Dec. 1, 2000.

International Search Report Application PCT/US03/01673 dated May 15, 2003.

* cited by examiner ions and methods of treating bacterial infections with the compounds.

BICYCLIC HETEROCYCLIC SUBSTITUTED PHENYL OXAZOLIDINONE ANTIBACTERIALS, AND RELATED COMPOSITIONS AND METHODS

CROSS-REFERENCE TO RELATED APPLICATIONS

This application is a continuation of U.S. Ser. No. 10/058,841, filed Jan. 28, 2002 now U.S. Pat. No. 6,608,081 which is a continuation-in-part to U.S. application Ser. No. 09/621,814 filed on Jul. 21, 2000 now U.S. Pat. No. 6,413,981 which claims the benefit of Provisional Application No. 60/148,621 filed Jul. 12, 1999.

FIELD OF THE INVENTION

The present invention relates to the field of phenyl oxazolidinone compounds having antibacterial activity against Gram-positive and Gram-negative bacteria, pharmaceutical compositions containing the compounds, and methods of treating bacterial infections with the compounds.

BACKGROUND OF THE INVENTION

Oxazolidinones have been identified, within the last twenty years, as a new class of antibacterials which are active against numerous multidrug-resistant gram positive organisms. Particularly problematic pathogens include methicillin-resistant *Staphylococcus aureus* (MRSA), glycopeptide-intermediate resistant *Staphylococcus aureus* (GISA), vancomycin-resistant enterocci (VRE) and penicillin- and cephalosporin-resistant *Streptococcus pneumoniae*. As a class, oxazolidinones exhibit a unique mechanism of action. Studies have shown that these compounds selectively bind to the 50S ribosomal subunit and inhibit bacterial translation at the initiation phase of protein synthesis. Exemplary members of oxazolidinones are linezolid (see WO 95/07271) and eperezolid.

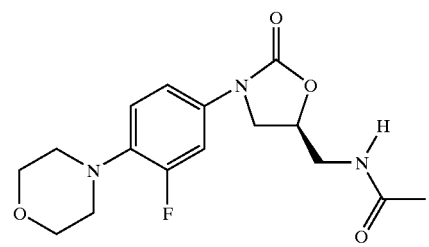

linezolid

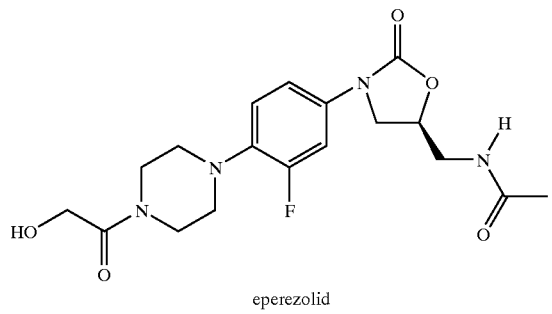

eperezolid

U.S. Pat. No. 5,792,765 to Riedl et al. discloses a series of substituted oxazolidinones (cyanoguanidine, cyanoamidines, and amidines) useful as antibacterial medicaments.

U.S. Pat. No. 5,910,504 to Hutchinson discloses a series of hetero-aromatic ring substituted phenyl oxazolidinones, including indolyl substituted compounds useful as antibacterial agents.

WO 98/54161 (Hester et al.) discloses amides, thioamides, ureas, and thioureas which are antibacterial agents.

WO 95107271 (Barbachyn et al.) discloses oxazine and thiazine oxazolidinone derivatives such as linezolid and its analogs which are useful antimicrobial agents, effective against a number of human and veterinary pathogens, including gram-positive aerobic bacteria such as multiple-resistant staphylococci, streptococci and enterococci as well as anaerobic organisms such as Bacteroides spp. and Clostridia spp. species, and acid-fast organisms such as *Mycobacterium tuberculosis, Mycobacterium avium* and *Mycobacterium* spp.

WO 93/09103 (Barbachyn et al.) discloses substituted aryl- and heteroarylphenyloxazolidinones which are useful as antibacterial agents.

SUMMARY OF THE INVENTION

The invention provides phenyl oxazolidinone compounds of Formula I:

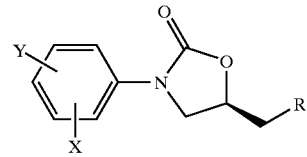

Formula I wherein:
R is selected from the group consisting of OH, O-Aryl, O-Heteroaryl, $N_3$, OR', $OSO_2R''$, —NR'''R'''', or

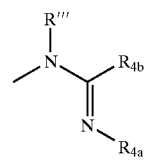

wherein:
(i) R' is straight-chain or branched acyl having up to 6 carbon atoms or benzyl;
(ii) R'' is straight-chain or branched alkyl, having up to 5 carbon atoms, phenyl or tolyl; and
(iii) R''' and R'''' are independently selected from the group consisting of H, cycloalkyl having 3 to 6 carbon atoms, phenyl or tert-butoxycarbonyl, fluorenyloxycarbonyl, benzyloxycarbonyl, straight-chain or branched alkyl having up to 6 carbon atoms which is optionally substituted by cyano or alkoxy-carbonyl having up to 4 carbon atoms, $-CO_2-R_1$, $-CO-R_1$, $-CS-R_1$, and $-SO_2-R_4$, in which
$R_1$ is selected from the group consisting of H, cycloalkyl having 3 to 6 carbon atoms, trifluoromethyl or phenyl, benzyl or acyl having up to 5 carbon atoms, straight-chain or branched alkyl having up to 6 carbon atoms, said alkyl optionally substituted by straight-chain or branched alkoxy-carbonyl having up to 5 carbon atoms, OH, cyano, up to 3 halogen atoms, and $-NR_5R_6$ in which $R_5$ and $R_6$ are identical or different and are selected from H, phenyl or straight-chain or branched alkyl having up to 4 carbon atoms;
$R_4$ is selected from straight-chain or branched alkyl having up to 4 carbon atoms or phenyl and:

$R_{4a}$ is CN, $COR_{4c}$, $COOR_{4c}$, $CONHR_{4c}$, CO—$NR_{4c}R_{4d}$, $SO_2R_{4c}$, or $NO_2$;

$R_{4b}$ is H, alkyl, $OR_{4c}$, $SR_{4c}$, amino, $NHR_{4c}$, $NR_{4c}R_{4d}$;

$R_{4c}$ and $R_{4d}$ are independently selected from H, alkyl, aryl, or in the case of any $NR_{4c}R_{4d}$ group $R_{4c}$ and $R_{4d}$ taken together with the nitrogen atom to which they are attached form a unsubstituted or substituted pyrrolidinyl, piperidinyl or morpholinyl group;

X is 0 to 4 members independently selected from the group consisting of halogen, OH, nitro, $C_{1-8}$ alkoxy, $C_{1-8}$ alkyl-amino, di($C_{1-8}$-alkyl-)amino, carboxy, alkoxycarbonyl, $C_{1-8}$ alkyl-CO—O—, $C_{1-8}$ alkyl-CO—NH—, carboxamide, CN, amine, $C_{3-6}$ cycloalkyl, $C_{1-8}$ alkyl optionally substituted with one or more members selected from the group consisting of F, Cl, OH; and Y is a radical of Formulae II or III:

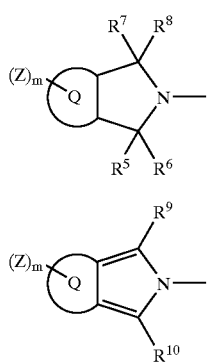

Formula II

Formula III wherein $R_5$, $R_6$, $R_7$, and $R_8$ are each independently H, alkyl, CN, nitro, $C_{1-8}$ alkyl, halo-$C_{1-8}$-alkyl, formyl, carboxy, alkoxycarbonyl, carboxamide, or $R_5$ and $R_6$ and/or $R_7$ and $R_8$ together form an oxo group;

$R_9$, and $R_{10}$ are each independently H, halogen, alkyl, OH, CN, nitro, $C_{1-8}$ alkyl, halo-$C_{1-8}$-alkyl, $C_{1-8}$ alkoxyl, amino, $C_{1-8}$-alkyl-amino, di($C_{1-8}$-alkyl-)amino, formyl, carboxy, alkoxycarbonyl, $C_{1-8}$-alkyl-CO—O—, $C_{1-8}$-alkyl-CO—NH—, carboxamide, or amine;

Q is a fused phenyl ring or a five- or six-membered heteroaromatic ring having one to four members selected from the group consisting of S, O, and N;

Z is halogen, alkyl, substituted-alkyl, aryl, substituted-aryl, heteroaryl, substituted-heteroaryl, CN, CHO, COalkyl, amino, alkoxy, HNCO—($C_1$-$C_8$alkyl), allyl, propargyl, allenyl, or N-alkylthiocarbamoyl; and m is 0 or 1, and the pharmaceutically acceptable salts and esters thereof.

Compounds of the above formula are useful as antibacterial agents for the treatment of bacterial infections in humans and animals.

The present invention is also directed to a method of treating a subject having a condition caused by or contributed to by bacterial infection, which comprises administering to said mammal a therapeutically effective amount of the compound of Formula I.

The present invention is further directed to a method of preventing a subject from suffering from a condition caused by or contributed to by bacterial infection, which comprises administering to the subject a prophylactically effective dose of the pharmaceutical composition of a compound of Formula I.

Other objects and advantages will become apparent to those skilled in art from a review of the ensuing specification.

DETAILED DESCRIPTION

Relative to the above description of the phenyl oxazolidinone compounds of the present invention, the following definitions apply.

Unless specified otherwise, the terms "alkyl", "alkenyl", and "alkynyl" may be straight or branched groups with 1–8 carbon atoms.

"Substituted alkyl" may be a straight or branched-chain moiety with 1–8 carbon atoms having one or more substituents selected from the group consisting of amino, dialkylamino, cycloalkyl, hydroxy, oxo, alkoxycarbonyl, benzyloxy, arylthio, alkylthio, hydroxyalkylthio, alkylsulfinyl, alkylsulfonyl, carboxy, phosphonooxy, dialkylphosphonooxy, dibenzylphosphonooxy, cyano, halo, trialkylsilyl, dialkylphenylsilyl, aryl, heteroaryl, heterocyclo, heterocyclomethylbenzoyloxy, dialkylaminomethylbenzoyloxy, dialkylaminoalkylcarbonyloxy, benzyloxycarbonylaminoalkylcarbonyloxy, and aminoalkylcarbonyloxy.

"Acyl" means an organic radical having the designated number of carbon atoms, derived from an organic acid by the removal of a hydroxyl group having the formula RCO, as in the case of acetyl where R is $CH_3$.

"Aryl" is an unsubstituted carbocyclic aromatic group including, but not limited to, phenyl, 1- or 2-naphthyl and the like. "Heteroaryl" refers to a cyclic aromatic radical having from five to ten atoms in the ring; where one to three ring atoms are independent heteroatoms such as S, O, and N, and the remaining ring atoms are carbon, for example, a pyridinyl, pyrazinyl, pyrimidinyl, pyrroyl, pyrazolyl, imidazolyl, thiazolyl, oxazolyl, isoxazolyl, thiadiazolyl, oxadiazolyl, thienyl, furanyl, quinolinyl, or isoquinolinyl, radical and the like.

"Substituted aryl" or "substituted heteroaryl" refers to an aryl or heteroaryl substituted by independent replacement of 1–3 of the hydrogen atoms thereon with halogen, OH, CN, mercapto, nitro, $C_{1-8}$-alkyl, halo-$C_{1-8}$-alkyl, $C_{1-8}$-alkoxy, thio-$C_{1-8}$-alkyl, amino, $C_{1-8}$-alkyl-amine, di($C_1$-$C_8$-alkyl-)amino, formyl, carboxy, alkoxycarbonyl, $C_{1-8}$-alkyl-CO—O—, $C_{1-8}$-alkyl-CO—NH—, or carboxamide. Further, substituted-heteroaryl may be substituted with a mono-oxo to give, for example, a 4-oxo-1-H-quinoline. Substituted-heteroaryl may also be substituted with a substituted-aryl or a second substituted-heteroaryl to give, for example, a 4-phenyl-imidazol-1-yl or a 3-pyridinyl-imidazol-1-yl, and the like.

The terms "heterocycle," "heterocyclic," and "heterocyclo" refer to an optionally substituted, fully saturated, partially saturated, or non-aromatic cyclic group which is, for example, a 3- to 7-membered monocyclic, 7- to 11-membered bicyclic, or 10- to 15-membered tricyclic ring system, which has at least one heteroatom in at least one carbon atom containing ring. Each ring of the heterocyclic group containing a heteroatom may have 1, 2, or 3 heteroatoms selected from nitrogen atoms, oxygen atoms, and sulfur atoms, where the nitrogen and sulfur heteroatoms may also optionally be oxidized. The nitrogen atoms may optionally be quaternized. The heterocyclic group may be attached at any heteroatom or carbon atom.

The term "halo" or "halogen" means fluoro, chloro, bromo and iodo. (mono-, di-, tri-, and per-) halo-alkyl is an alkyl radical substituted by independent replacement of the hydrogen atoms thereon with halogen. P denotes phosphorus.

The compounds of the instant invention are asymmetric in the oxazolidinone ring at the 5- position and thus exist as optical antipodes. As such, all possible optical antipodes, enantiomers or diastereomers resulting from additional asymmetric centers that may exist in optical antipodes, racemates and racemic mixtures thereof are also part of this invention. The antipodes can be separated by methods known to those skilled in the art such as, for example, fractional recrystallization of diastereomeric salts of enantiomerically pure acids. Alternatively, the antipodes can be separated by chromatography on a Pirkle column.

The phrase "pharmaceutically acceptable salts" denotes salts of the free base which possess the desired pharmacological activity of the free base and which are neither biologically nor otherwise undesirable. These salts may be derived from inorganic or organic acids. Examples of inorganic acids are hydrochloric acid, nitric acid, hydrobromic acid, sulfuric acid, or phosphoric acid. Examples of organic acids are acetic acid, propionic acid, glycolic acid, lactic acid, pyruvic acid, malonic acid, succinic acid, malic acid, maleic acid, fumaric acid, tartaric acid, citric acid, benzoic acid, cinnamic acid, mandelic acid, methanesulfonic acid, ethanesulfonic acid, p-toluenesulfonic acid, methyl sulfonic acid, salicyclic acid and the like. Suitable salts are furthermore those of inorganic or organic bases, such as KOH, NaOH, Ca(OH)$_2$, Al(OH)$_3$, piperidine, morpholine, ethylamine, triethylamine and the like.

Also included within the scope of the invention are the hydrated forms of the compounds which contain various amounts of water, for instance, the hydrate, hemihydrate and sesquihydrate forms.

The term "subject" includes, without limitation, any animal or artificially modified animal. In the preferred embodiment, the subject is a human.

The term "drug-resistant" or "drug-resistance" refers to the characteristics of a microbe to survive in presence of a currently available antimicrobial agent at its routine, effective concentration.

The compounds of the present invention possess antibacterial activity against Gram-positive and certain Gram-negative bacteria. They are useful as antibacterial agents for the treatment of bacterial infections in humans and animals. Particularly, these compounds have antimicrobial activity against S. aureus, S. epidermidis, S. pneumoniae, E. faecalis, E. faecium, Moraxella catarrhalis, and H. influenzae. More particularly, these compounds are useful against resistant bacteria such as MRSA and GISA, and have a low susceptibility to acquired resistance mechanisms.

Compounds of Formula I which are preferred for such purposes are those in which R is any of the following:

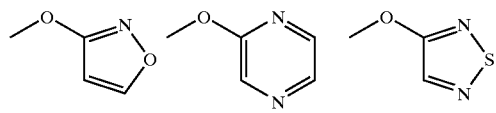

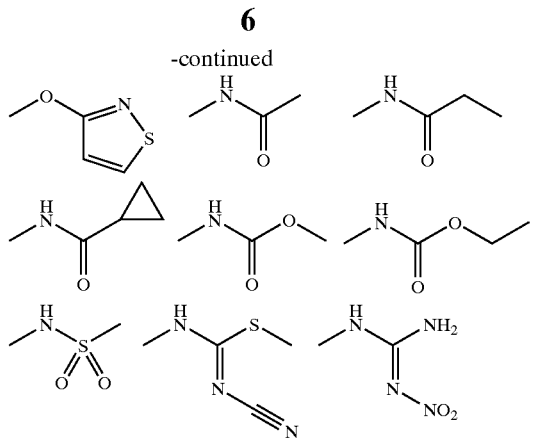

In addition Compounds of Formula I which are preferred for such purposes are those in which Y is any of the following:

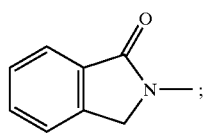

isoindolone-

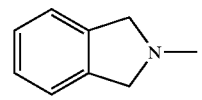

(1,3-dihydro-2H-isoindol-2-yl)-

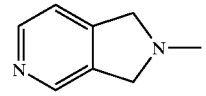

(1,3-dihydro-2H-pyrrolo[3,4-c]pyridin-2-yl)-

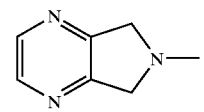

(5,7-dihydro-6H-pyrrolo[3,4-b]pyrazin-6-yl)-

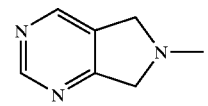

(5,7-dihydro-6H-pyrrolo[3,4-d]pyrimidin-6-yl)-

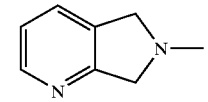

(5,7-dihydro-6H-pyrrolo[3,4-b]pyrimidin-6-yl)-

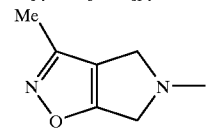

4,6-dihydro-3-methyl-5H-pyrrolo[3,4-d]isoxazol-5-yl)-

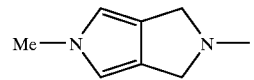

(3,5-dihydro-5-methylpyrrolo[3,4-c]pyrrol-2(1H)-yl)-

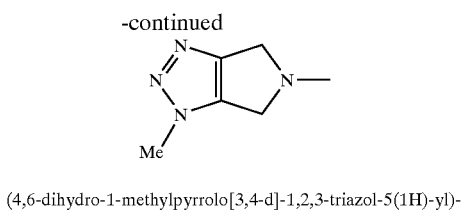

(4,6-dihydro-1-methylpyrrolo[3,4-d]-1,2,3-triazol-5(1H)-yl)-

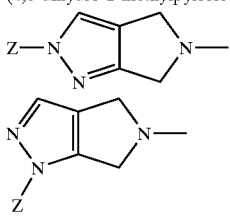

In addition, Compounds of Formula I which are preferred for such purposes or those in which Z is any of the following: propargyl, allyl, allenyl, N-alkylthiocarbamoyl, alkyl, heteroaryl, substituted-heteroaryl, or a substituted alkyl having one or more substituents selected form the group consisting of amino, dialkylamino, cycloalkyl, hydroxy, oxo, alkoxycarbonyl, benzyloxy, arylthio, alkylthio, hydroxyalkylthio, alkylsulfinyl, alkylsulfonyl, carboxy, phosphonooxy, dialkylphosphonooxy, dibenzylphosphonooxy, cyano, halo, trialkylsilyl, dialkylphenylsilyl, aryl, heteroaryl, heterocyclo, heterocyclomethylbenzoyloxy, dialkylaminomethylbenzoyloxy, dialkylaminoalkylcarbonyloxy, benzyloxycarbonylaminoalkylcarbonyloxy, and aminoalkylcarbonyloxy.

Particularly preferred Compounds of Formula I are those wherein Z is selected from the group consisting of propargyl, allyl, allenyl, N-alkylthiocarbamoyl, ethyl, isopropyl, t-butyl, 2-hydroxyethyl, 3-hydroxypropyl, 2,2,2-trifluoroethyl, cyanomethyl, 2-cyanoethyl, cyclopropylmethyl, 2-oxopropyl, methylthiomethyl, 2-methylthioethyl, methylsulfonylmethyl, 2-methylsulfonylethyl, methylsulfinylmethyl, t-butoxycarbonylmethyl, 2-carboxyethyl, 2-(di-t-butylphosphonooxy)ethyl, 2-(dibenzylphosphonooxy)ethyl, 2-phosphonooxyethyl, 2-aminoethyl, 2-(diethylamino)ethyl, 2-(dimethylamino)ethyl, 2-(4-morpholinyl)ethyl, 2-(4-thiomorpholinyl)ethyl, trimethylsilylmethyl, dimethylphenylsilylmethyl, benzyloxymethyl, benzyl, 5-tetrazolylmethyl, 3-pyridylmethyl, 2-pyridylmethyl, 2-oxiranylmethyl, 2-oxooxazolidin-5-ylmethyl, 2,3-dihydroxypropyl, 2-hydroxy-3-(1-piperidinyl)propyl, 2-hydroxy-3-(4-morpholinyl)propyl, 2-hydroxy-3-phenylthiopropyl, 2-hydroxy-3-ethylthiopropyl, 2-hydroxy-3-(2-hydroxyethylthio)propyl, 3-[4-(1,1-dioxothiomorpholinyl)]-2-hydroxypropyl, 3-ethylsulfinyl-2-hydroxypropyl, 2-[4-(4-morpholinylmethyl)benzoyloxy]ethyl, 2-[4-(dimethylaminomethyl)benzoyloxy]ethyl, 2-[4-(4-methyl-1-piperazinylmethyl)benzoyloxy]ethyl, 2-(dimethylaminoacetoxy)ethyl, 2-[2-(benzyloxycarbonylamino)-3-methylbutyryloxy]ethyl, 2-(2-amino-3-methylbutyryloxy)ethyl, 2-pyridinyl, pyridazinyl, and 2-pyrimidinyl.

Particular examples of the present invention include the following compounds:

N-[[(5S)-3-[4-(1,3-Dihydro-2H-isoindol-2-yl)-3-fluorophenyl]-2-oxo-5-oxazolidinyl]methyl]acetamide;

N-[[(5S)-3-[4-(1,3-Dihydro-2H-pyrrolo[3,4-c]pyridin-2-yl)-3-fluorophenyl]-2-oxo-5-oxazolidinyl]methyl]acetamide;

N-[[(5S)-3-[3-Fluoro-4-(5-oxido-2H-pyrrolo[3,4-c]pyridin-2-yl)phenyl]-2-oxo-5-oxazolidinyl]methyl]acetamide;

N-[[(5S)-3-[4-(5,7-dihydro-6H-pyrrolo[3,4-b]pyridin-6-yl)-3-fluorophenyl]-2-oxo-5-oxazolidinyl]methyl]acetamide;

N-[[(5S)-3-[4-(1,3-dihydro-1-oxo-2H-isoindol-2-yl)-3-fluorophenyl]-2-oxo-5-oxazolidinyl]methyl]acetamide; and (5R)-3-[4-(5,7-Dihydro-6H-pyrrolo[3,4-b]pyridin-6-yl)-3-fluorophenyl]-5-(hydroxymethyl)-2-oxazolidinone;

N-[[(5S)-3-[4-[2,6-dihydro-2-(2-hydroxyethyl)pyrrolo[3,4-c]pyrazol-5(4H)-yl]-3-fluorophenyl]-2-oxo-5-oxazolidinyl]methyl]acetamide;

N-[[(5S)-3-[4-[2,6-dihydro-2-[(2R)-2,3-dihydroxypropyl]pyrrolo[3,4-c]pyrazol-5(4H)-yl]-3-fluorophenyl]-2-oxo-5-oxazolidinyl]methyl]acetamide;

N-[[(5S)-3-[4-[2,6-dihydro-2-[(2S)-2,3-dihydroxypropyl]pyrrolo[3,4-c]pyrazol-5(4H)-yl]-3-fluorophenyl]-2-oxo-5-oxazolidinyl]methyl]acetamide;

N-[[(5S)-3-[4-(2,6-dihydro-2-propargylpyrrolo[3,4-c]pyrazol-5(4H)-yl)-3-fluorophenyl]-2-oxo-5-oxazolidinyl]methyl]acetamide;

N-[[(5S)-3-[4-(2,6-dihydro-2-cyanomethylpyrrolo[3,4-c]pyrazol-5(4H)-yl)-3-fluorophenyl]-2-oxo-5-oxazolidinyl]methyl]acetamide;

The compounds of Formula I that are the subject of this invention may be prepared from readily available starting materials such as isoindole (Gawley et al., *J. Org. Chem.*, 1988, 53:5381), 6,7-dihydro-5H-pyrrolo[3,4-c]pyridine and 6,7-dihydro-5H-pyrrolo[3,4-b]pyridine (U.S. Pat. No. 5,371,090 to Petersen et al.) in accordance with synthetic methods well known in the art. Representative procedures are outlined in Scheme I–V:

Scheme I

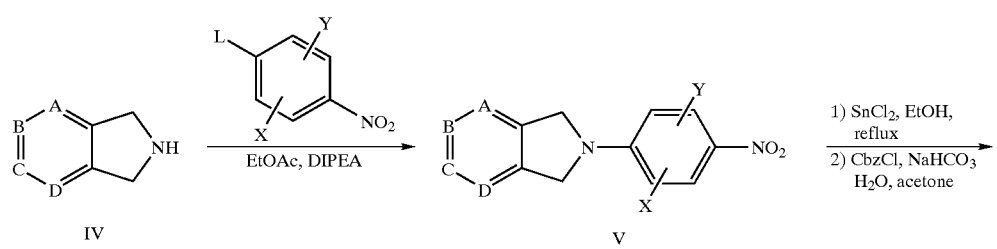

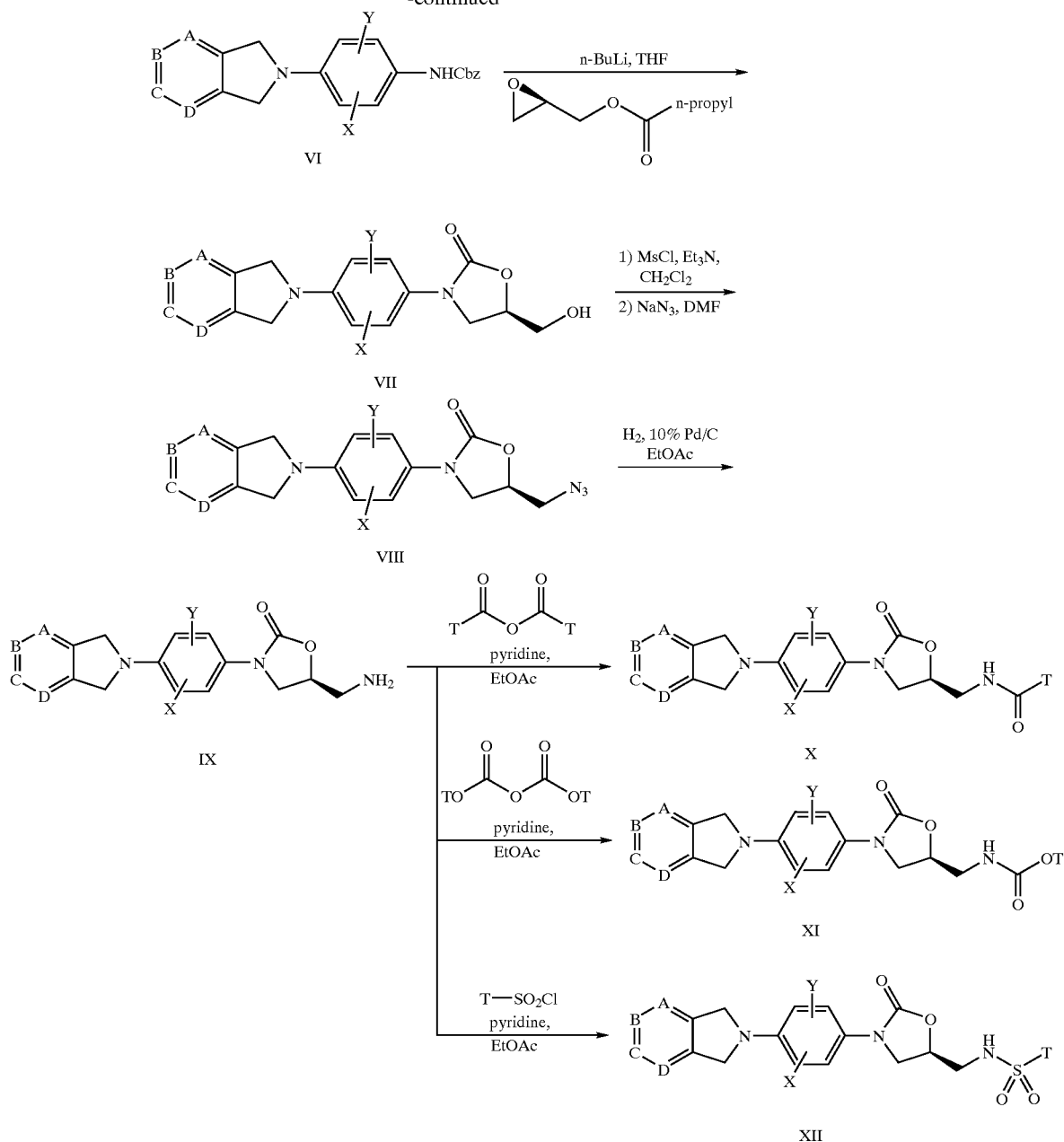

In accordance with Scheme I, bicyclic heterocycles of general formula IV are treated with a substituted nitrobenzene derivative (L is an appropriate leaving group such as a halogen of trifluoromethanesulfonyloxy) in a suitable base and solvent such as diisopropylamine and ethyl acetate, to give the substituted nitrophenyl compound V.

The nitrobenzene derivative V is then reduced to the aniline by an appropriate reaction, for instance by treatment with SnCl$_2$ or by catalytic hydrogenation in the presence of a suitable catalyst, such as palladium on carbon. The aniline is then treated with benzyl or methyl chloroformate and sodium bicarbonate to form the corresponding benzyl or methyl carbamate derivative VI.

The Cbz aniline VI is then deprotonated with a lithium base such as n-butyllithium and reacted with (R)- glycidyl butyrate to afford the oxazolidinone VII. The hydroxymethyl group can then be converted to an amide as shown in Scheme I by preparation of the mesylate, conversion to azide VIII, and reduction to amine IX by an appropriate procedure such as hydrogenation. Alternatively displacement of a mesylate (Scheme II) or appropiate leaving group such as tosylate or chlorine with potassium phthalimide and removal of the phthaloyl protecting group by hydrazinolysis would provide amine IX. The amine IX can be converted to amide X by an acylation reaction using techniques known in the art, such as treatment with acetic anhydride in the presence of a base such as pyridine. Alternatively, amine IX can be converted to a carbamate XI by treatment with methylchloroformate and pyridine, or reacted with a sulfonyl chloride in an inert solvent in the presence of an organic base like pyridine to form a sulfonamide XII

Scheme II

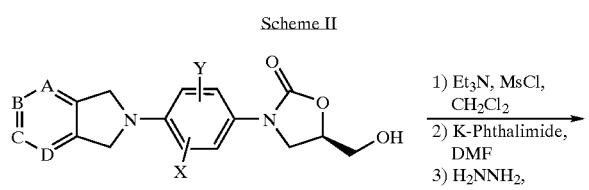

Furthermore, by treating VII with a suitable, non-nucleophilic base, for example NaH, the displacement of a leaving group (LG), such as chlorine or bromine, can be effected from an appropriately reactive aza-heterocycle (LG-Het)(Scheme III).

Scheme IV

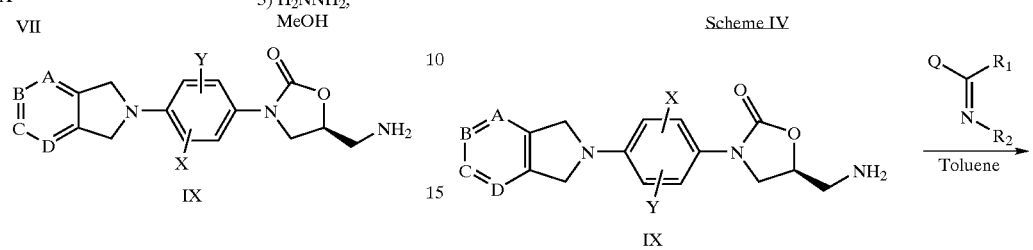

Scheme III

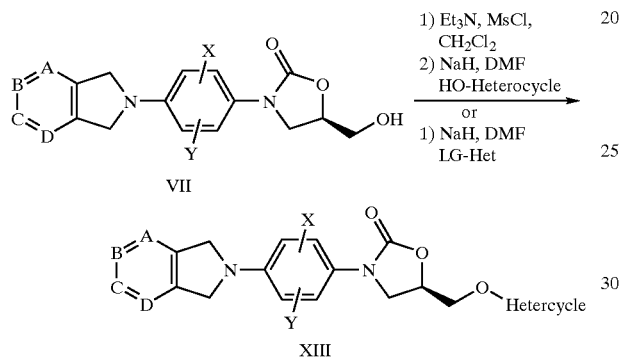

For the formation of oxazolidione in which R=O-Heteroaryl (XIII), the oxazolidinone carbinol VII can be converted to the corresponding mesylate or other appropri- Compounds of structure XIV can be prepared as shown in Scheme IV. Amine IX can be converted to various functionalized amidines by reaction with activated imines, where Q is a leaving group such as methylthio or methoxy, in a suitable solvent, for example toluene or methanol, with or without a catalyst (such $AgNO_3$) present at a temperature range of 0–110° C.

Scheme V

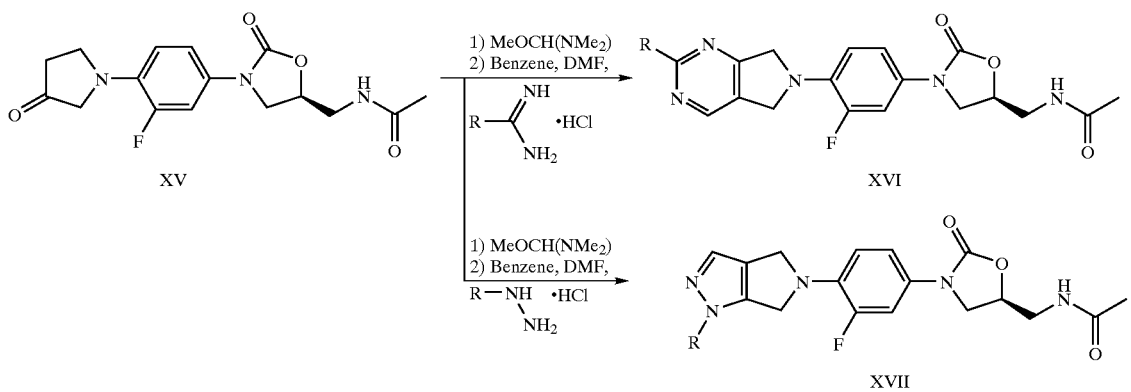

ate leaving group and reacted with HO-Het (a suitible hydroxyl containing heterocycle), either in the presence of base or with HO-Het as a preformed alkoxide, in an appropriate solvent, for example DMF or acetonitrile (Scheme III). Alternatively, Mitsunobu conditions can be used to couple VII with HO-Heterocycle by treating with triphenylphosphine and diisopropyl azodicarboxylate (DIAD) in an appropriate solvent, such as THF, at a suitable temperature, preferably room temperature. Reaction conditions and leading references can be found in Gravestock et al, WO99/64416.

In accordance with Scheme V pyrrolidinone XV (prepared as in WO96/13502) is first reacted with methoxy-bis(dimethylamine) or other activated dimethylformamide reagent and, second, heated in a suitable solvent (for example DMF and benzene) with either substituted amidines, to form pyrrolopyrimidines oxazolidinones such as XVI, or substituted hydrazines, to form pyrrolopyrazole oxazolidinones such as XVII. Formation of the—enamine, alkoxymethylene or alkoxycarbonyl derivatives of pyrrolidinone XV, according to Brighty et al in U.S. Pat. No. 5,037,834A, would also allow access to these systems.

Scheme VI

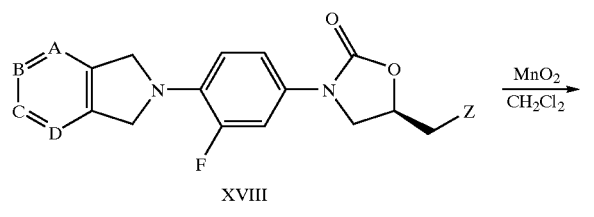

As shown in Scheme VI compounds with the structure XIX can be achieved by oxidation of the various compounds, XVIII, using an appropriate oxidant (for example manganese dioxide, peroxyacetic acid, DDQ or air) in a suitable solvent such as methylene chloride.

Scheme VII

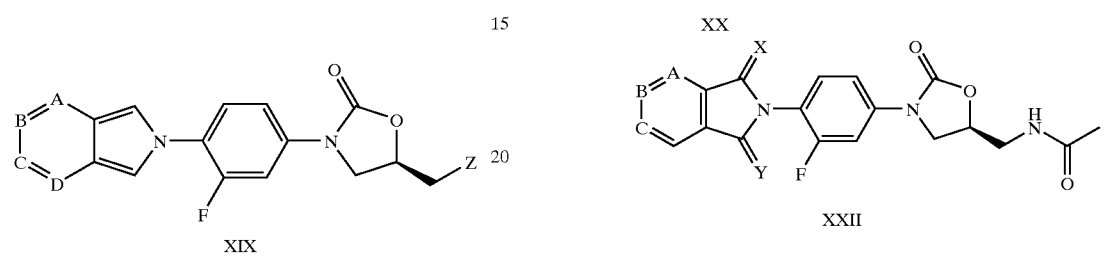

Oxo-derivatives of structure XXII in Scheme VII, (X=O, Y=H$_2$ or X=H$_2$, Y=O) can be constructed by reacting 1,2-aryl dicarboxaldehydes (where XXI, U=H) with aniline XX (prepared as in WO96/23788) in the presence of acids, such as acetic acid, in a suitable solvent such as methylene chloride. The di-oxo-derivatives (structure XXII where X=Y=O) are prepared from the reaction of aniline XX with selected 1,2-aryl dicarbonyl reagents with a suitable leaving group (XXI where U=Cl, Br, etc).

Scheme VIII

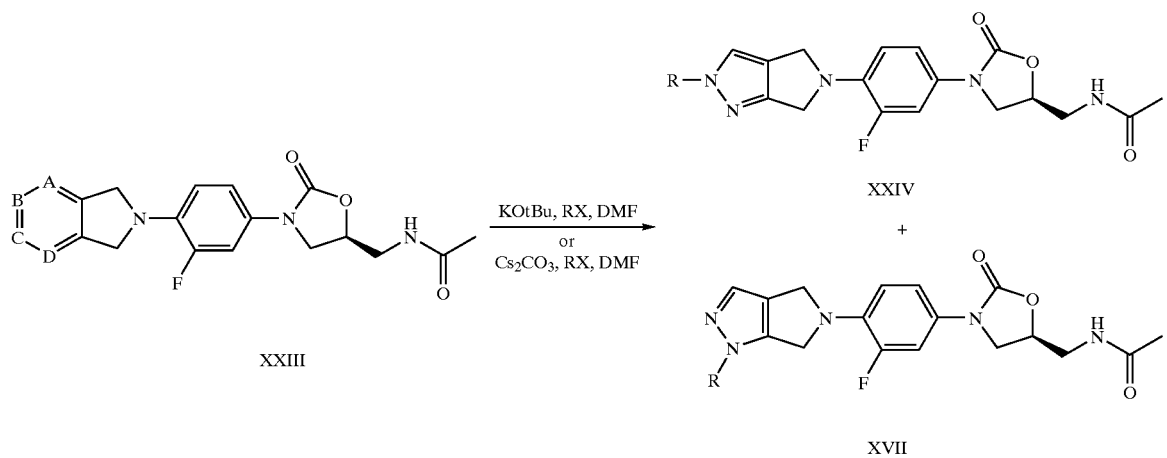

Compounds of the structure XXIV and XVII can be prepared as shown in Scheme VIII. Pyrazole XXIII can be converted to regioisomeric alkylated pyrazoles by reaction with a base, such as potassium tert-butoxide, sodium hydride, or cesium carbonate, and an alkylating agent, such as an alkyl halide.

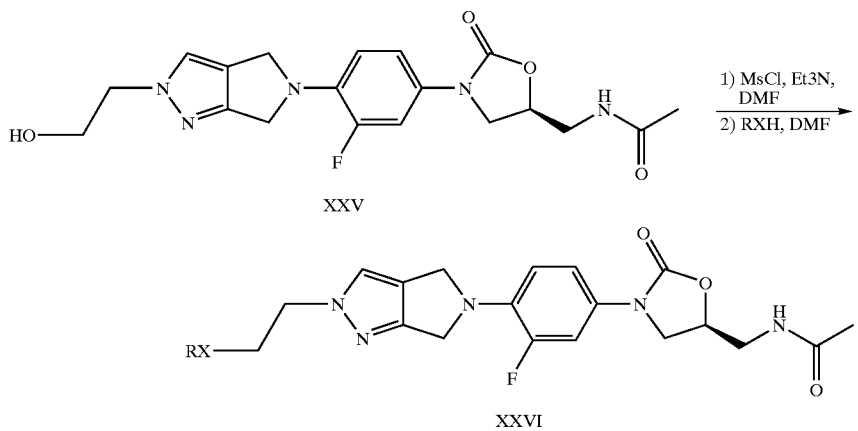

Scheme IX

Pyrazole XXV can be further functionalized (Scheme IX) by conversion of the hydroxyl group to an appropriate leaving group, such as mesylate or halide, and displacement with nucleophiles, such as an amine, thiol, etc to afford substituted pyrazoles such as XXVI where X represents nitrogen, sulfur, etc.

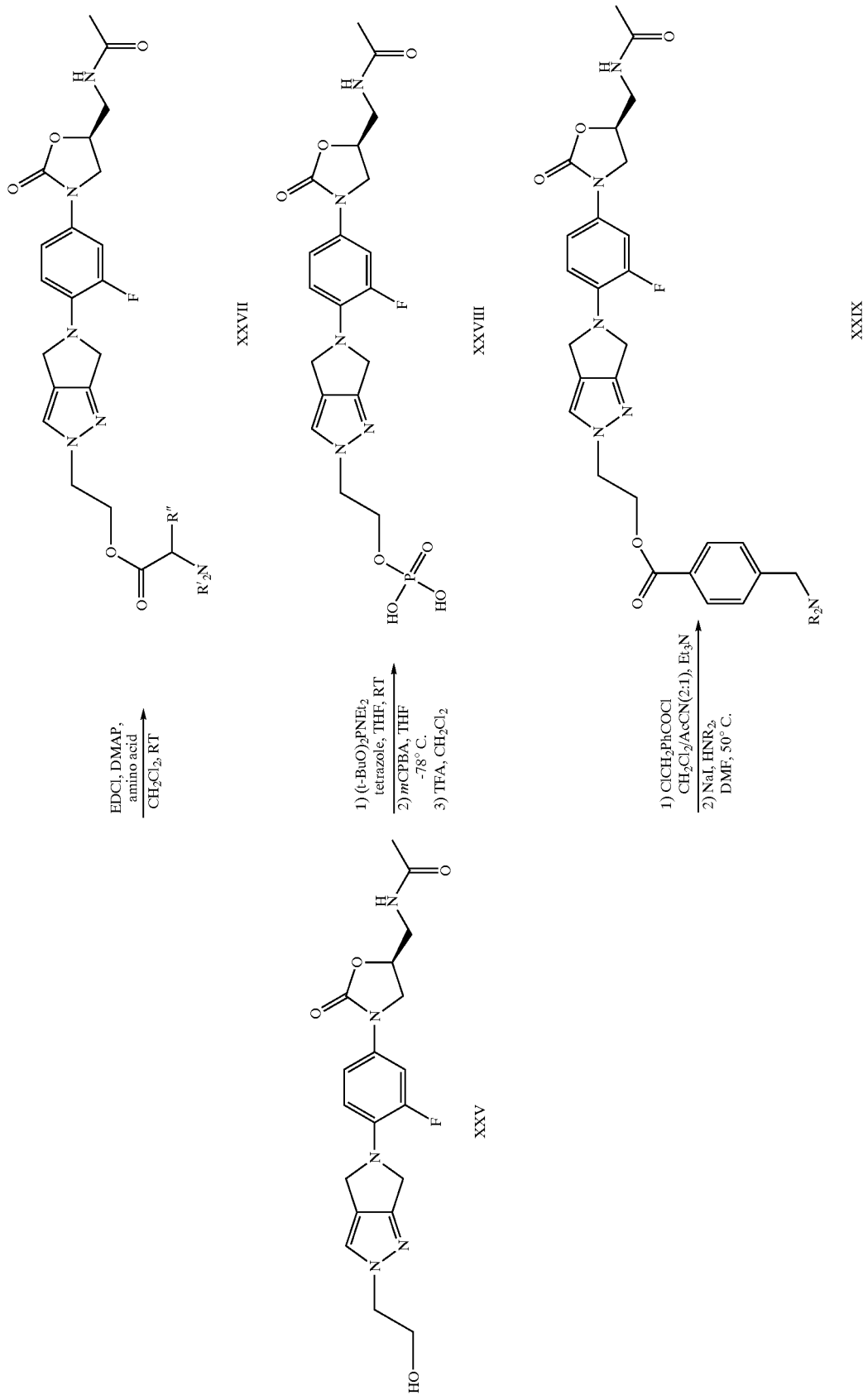

Various derivatives [amino acid (XXVII), phosphate (XXVIII) and substituted benzoic acid (XXIX)] with greater aqueous solubility can be prepared as illustrated in Scheme X. Coupling of pyrazole XXV with an amino acid derivative can be accomplished using a coupling reagent, such as EDCI and DMAP. Following coupling, the amino acid protecting groups can be remove (if so desired) by standard literature methods known to those skilled in the art. Phosphate derivative XXVIII can be prepared by a three-step procedure via reaction of pyrazole XXV with dialkyl(dialkylamino)phosphite and tetrazole, oxidation of the phosphorous with meta-chloroperoxybenzoic acid and removal of tert-butyl protecting groups with acid, such as TFA in methylene chloride. Water soluble benzoic acid derivative XXIX can be prepared by initial coupling of pyrazole XXV with 2-(chloromethyl)benzoyl chloride, utilizing triethyl amine as base, and then displacement of the halide with an amine, such morpholine, dimethylamine and the like, employing sodium iodide as a catalyst.

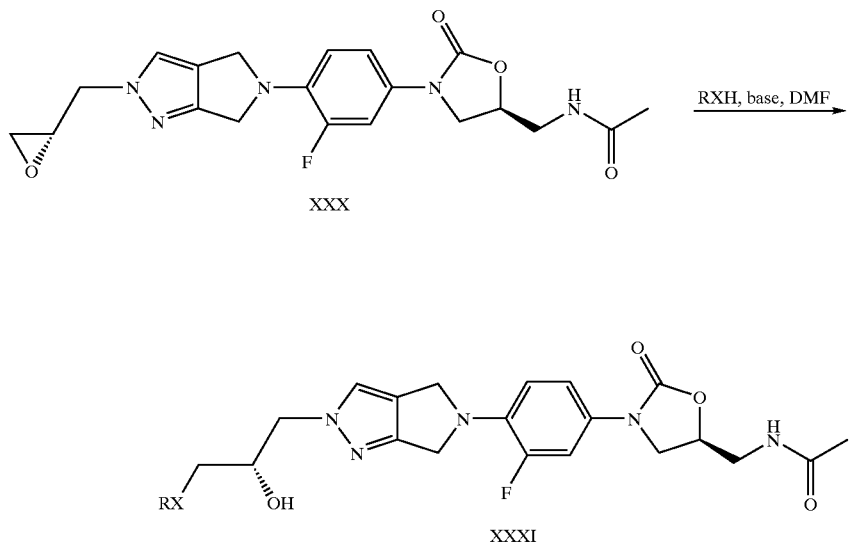

Substituted 2-hydroxy propyl pyrazoles can be prepared through attack on the epoxide functionality of Compound XXX with various nucleophiles, such an amine, thiol, etc. to provide pyrazoles such as XXXI where X represents nitrogen, sulfur, etc (Scheme XI). The sulfur containing analogs, represented by Compound XXXII where X represents an inert linking group (Scheme XII), can be further functionalized by reaction with oxidizing agent, such as meta-chloroperoxybenzoic acid or tetrabutylammonium oxone, to provide sulfoxide or sulfone analogs, such as XXXIII.

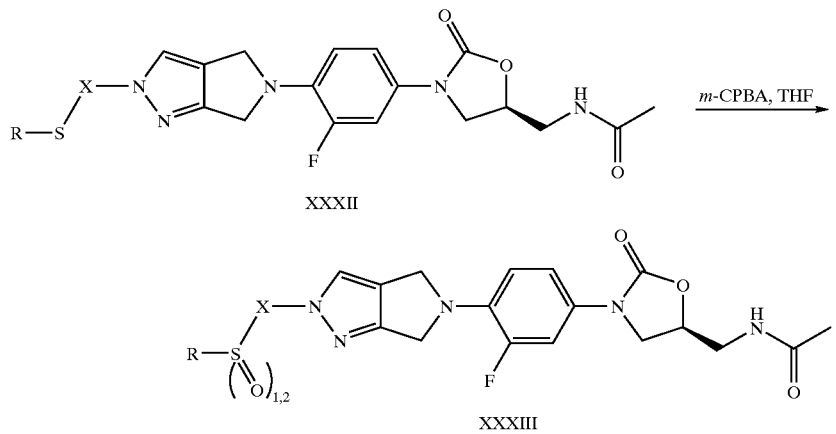

Tetrazole XXXV can be prepared by reaction of nitrile XXXIV with azidotrimethylsilane and catalytic dibutyltinoxide provides tetrazole (Scheme XIII).

Scheme XIII

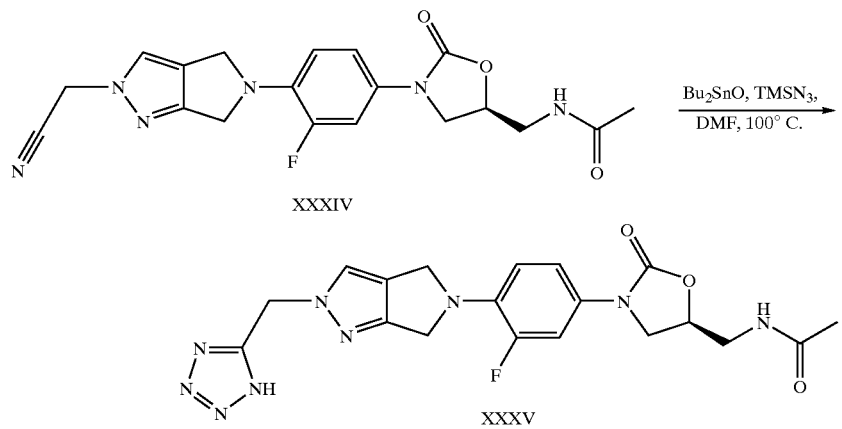

Definitions

All temperatures are in degrees Centigrade

Brine refers to an saturated aqueous sodium chloride solution

DMF refers to N,N-dimethylformamide

THF refers to tetrahydrofuran

Cbz refers to carbobenzyloxy n-BuLi refers to n-butyl lithium

MS refers to mass spectrometry expressed as mile or mass/charge unit

[M+H] refers to the positive ion of a parent plus a hydrogen atom

Ether refers to diethyl ether

RT refers to room temperature

Mp refers to melting point $CH_2Cl_2$ refers to methylene chloride

NaOH refers to sodium hydroxide

MeOH refers to methanol

EtOAc refers to ethyl acetate ppt refers to a precipitate

These compounds have antimicrobial activity against susceptible and drug resistant bacterial pathogens such as S. aureus, S. epidermidis, S. pneumoniae, S. pyogenes, Enterococcus spp., Moraxella catarrhalis and H. influenzae. These compounds are particularly useful against drug resistant Gram-positive cocci such as methicillin-resistant S. aureus and vancomycin-resistant enterococci. These compounds are useful in the treatment of community-acquired pneumonia, upper and lower respiratory tract infections, skin and soft tissue infections, hospital-acquired lung infections, bone and joint infections, and other bacterial infections.

Minimal inhibitory concentration (MIC) has been an indicator of in vitro antibacterial activity widely used in the art. The in vitro antimicrobial activity of the compounds was determined by the microdilution broth method following the test method from the National Committee for Laboratory Standards (NCCLS). This method is described in the NCCLS Document M7-A4, Vol.17, No.2, "Methods for Dilution Antimicrobial Susceptibility Test for Bacteria that Grow Aerobically—Fourth Edition", which is incorporated herein by reference.

In this method two-fold serial dilutions of drug in cation adjusted Mueller-Hinton broth are added to wells in microdilution trays. The test organisms are prepared by adjusting the turbidity of actively growing broth cultures so that the final concentration of test organism after it is added to the wells is approximately $5\times10^4$ CFU/well.

Following inoculation of the microdilution trays, the trays are incubated at 35° C. for 16–20 hours and then read. The MIC is the lowest concentration of test compound that completely inhibits growth of the test organism. The amount of growth in the wells containing the test compound is compared with the amount of growth in the growth-control wells (no test compound) used in each tray. As set forth in Table 1, some compounds of the present invention were tested against a variety of pathogenic bacteria resulting in a range of activities, from 1 to $\geq 128$ µg/mL depending on the organism tested. S. aureus OC2878 is a MRSA and E. faecium OC3312 is a vancomycin resistant enterococcus.

TABLE 1

MIC Values of Some Compounds of Formula I

| Compound No. | MIC (mg/mL) in Test Strains | | |
|---|---|---|---|
| | S. aureus OC4172 | S. aureus OC2878 | E. faecium OC3312 |
| 1 | 2 | 2 | 2 |
| 2 | 2 | 1 | 4 |
| 3 | 0.5 | 0.25 | 0.5 |
| 4 | 1 | 0.5 | 1 |
| 5 | >32 | >32 | >32 |
| 6 | 64 | 32 | 32 |
| 7 | >32 | 8 | 16 |
| 8 | 8 | 4 | 8 |
| 9 | >32 | >32 | >32 |
| 10 | >32 | 8 | 64 |
| 11 | 2 | 1 | 2 |
| 12 | 8 | 2 | 4 |
| 13 | 2 | 1 | 2 |
| 14 | 32 | 16 | 16 |
| 15 | 2 | 2 | 2 |
| 16 | 8 | 8 | 8 |
| 17 | 4 | 2 | 2 |
| 18 | 16 | 16 | 16 |
| 19 | 8 | 4 | 8 |
| 20 | 4 | 2 | 4 |
| 21 | >64 | >64 | >64 |
| 22 | 2 | 2 | 2 |
| 23 | 8 | 8 | 8 |

TABLE 1-continued

MIC Values of Some Compounds of Formula I

| Compound No. | S. aureus OC4172 | S. aureus OC2878 | E. faecium OC3312 |
|---|---|---|---|
| 24 | 8 | 8 | 8 |
| 25 | 64 | >128 | 32 |
| 26 | 1 | 0.5 | 1 |
| 27 | 8 | 4 | 8 |
| 28 | 0.5 | 0.5 | 0.5 |
| 29 | >32 | 8 | 16 |
| 30 | >128 | >128 | >128 |
| 31 | >16 | >16 | >16 |
| 32 | 4 | 2 | 2 |
| 33 | 32 | 32 | 32 |
| 34 | 8 | 2 | 4 |
| 35 | 0.5 | 0.25 | 2 |
| 36 | 1 | 0.5 | 1 |
| 37 | 1 | 1 | 0.5 |
| 38 | 2 | 2 | 1 |
| 39 | 1 | 2 | 1 |
| 40 | 1 | 1 | 1 |
| 41 | 2 | 2 | 2 |
| 42 | 2 | 2 | 2 |
| 43 | 1 | 1 | 1 |
| 44 | 1 | 1 | 1 |
| 45 | 4 | 4 | 4 |
| 46 | 4 | 4 | 8 |
| 47 | 32 | 16 | 32 |
| 48 | 8 | 8 | 8 |
| 49 | 16 | 4 | 8 |
| 50 | 8 | 4 | 8 |
| 51 | 32 | 32 | 32 |
| 52 | 8 | 4 | 8 |
| 53 | 8 | 4 | 4 |
| 54 | 32 | 32 | 16 |
| 55 | 8 | 8 | 8 |
| 56 | 1 | 0.5 | 1 |
| 57 | 0.5 | 0.5 | 1 |
| 58 | 32 | 4 | 16 |
| 59 | 1 | 0.5 | 1 |
| 60 | 8 | 8 | 8 |
| 61 | 4 | 4 | 4 |
| 62 | 1 | 1 | 2 |
| 63 | 4 | 4 | 4 |
| 64 | 8 | 16 | 16 |
| 65 | 1 | 0.5 | 2 |
| 66 | 2 | 2 | 2 |
| 67 | 2 | 0.5 | 1 |
| 68 | 2 | 2 | 2 |
| 69 | 2 | 2 | 4 |
| 70 | 8 | 4 | 8 |
| 71 | 2 | 1 | 2 |
| 72 | 2 | 1 | 2 |
| 73 | 8 | 4 | 4 |
| 74 | 4 | 4 | 4 |
| 75 | 4 | 2 | 4 |
| 76 | 16 | 8 | 8 |
| 77 | 8 | 4 | 16 |
| 78 | 4 | 1 | 2 |
| 79 | 4 | 2 | 4 |
| 80 | 8 | 2 | 4 |
| 81 | 16 | 8 | 16 |
| 82 | 2 | 1 | 2 |
| 83 | >16 | 16 | 16 |
| 84 | 128 | 8 | 32 |
| 85 | 4 | 4 | 4 |
| 86 | 4 | 4 | 4 |
| 87 | >32 | >32 | >32 |
| 88 | 32 | 128 | 64 |
| 89 | 1 | 1 | 2 |
| 90 | 2 | 2 | 4 |
| 91 | 4 | 4 | 8 |
| 92 | 4 | 2 | 4 |
| 93 | 4 | 2 | 4 |
| 94 | 2 | 2 | 2 |
| 95 | 4 | 2 | 2 |
| 96 | 16 | 16 | 16 |
| 97 | 8 | 8 | 8 |
| 98 | 4 | 2 | 4 |
| 99 | 4 | 2 | 4 |
| 100 | 8 | 4 | 8 |
| 101 | 4 | 4 | 4 |
| 102 | 8 | 8 | 4 |
| 103 | 32 | 16 | 32 |
| 104 | 16 | 16 | 16 |
| 105 | 4 | 4 | 8 |
| 106 | 16 | 8 | 16 |
| 107 | 4 | 2 | 4 |
| 108 | 2 | 1 | 2 |
| 109 | 2 | 2 | 2 |
| 110 | 4 | 2 | 4 |
| 111 | 16 | 8 | 16 |
| 112 | 4 | 4 | 8 |
| 113 | 32 | 32 | >32 |
| 114 | 64 | 64 | 64 |
| 115 | 32 | 16 | 32 |
| 116 | 8 | 8 | 4 |
| 117 | 16 | 8 | 8 |
| 118 | 4 | 4 | 4 |
| 119 | 16 | 16 | 32 |
| 120 | 16 | 16 | 16 |

This invention further provides a method of treating bacterial infections, or enhancing or potentiating the activity of other antibacterial agents, in a subject having conditions caused by or contributed to by bacterial infection, which comprises administering to the animals a compound of the invention alone or in admixture with another antibacterial agent in the form of a medicament according to the invention. The terms of "treating" and "treatment" include administering, either simultaneously, separately or sequentially, a pharmaceutically effective amount of a composition containing one or more of the compounds disclosed herein to a subject that desires inhibition of bacterial growth. The pharmaceutically effective amount of the compound used to practice the present invention for treatment varies depending on the manner of administration, the age, weight, and general health of the subject treated, and ultimately will be decided by physicians or veterinarians.

The compounds of the present invention may be administered to a subject such as a human by any route appropriate to the condition to be treated, suitable routes including oral, rectal, nasal, topical (including buccal and sublingual), vaginal and parenteral (including subcutaneous, intramuscular, intravenous, intradermal, intrathecal and epidural). The preferred route may vary with, for example, the condition of the recipient as well as the ease of preparation and administration.

When the compounds are employed for the above utility, they may be combined with one or more pharmaceutically acceptable carriers, e.g., solvents, diluents, and the like, and may be administered orally in such forms as tablets, capsules, dispersible powders, granules, or suspensions containing for example, from about 0.5% to 5% of suspending agent, syrups containing, for example, from about 10% to 50% of sugar, and elixirs containing, for example, from about 20% to 50% ethanol, and the like, or parenterally in the form of sterile injectable solutions or suspensions containing from about 0.5% to 5% suspending agent in an isotonic medium. These pharmaceutical preparations may contain, for example, from about 0.5% up to about 90% of the active ingredient in combination with the carrier, more usually between 5% and 60% by weight.

Compositions for topical application may take the form of liquids, creams or gels, containing a therapeutically effective concentration of a compound of the invention admixed with a dermatologically acceptable carrier.

In preparing the compositions in oral dosage form, any of the usual pharmaceutical media may be employed. Solid carriers include starch, lactose, dicalcium phosphate, microcrystalline cellulose, sucrose and kaolin, while liquid carriers include sterile water, polyethylene glycols, non-ionic surfactants and edible oils such as corn, peanut and sesame oils, as are appropriate to the nature of the active ingredient and the particular form of administration desired. Adjuvants customarily employed in the preparation of pharmaceutical compositions may be advantageously included, such as flavoring agents, coloring agents, preserving agents, and antioxidants, for example, vitamin E, ascorbic acid, BHT and BHA.

The preferred pharmaceutical compositions from the standpoint of ease of preparation and administration are solid compositions, particularly tablets and hard-filled or liquid-filled capsules. Oral administration of the compounds is preferred. These active compounds may also be administered parenterally or intraperitoneally. Solutions or suspensions of these active compounds as a freebase or pharmacological acceptable salt can be prepared in water suitably mixed with a surfactant such as hydroxypropyl-cellulose. Dispersions can also be prepared in glycerol, liquid polyethylene glycols and mixtures thereof in oils. Under ordinary conditions of storage and use, these preparations may contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), suitable mixtures thereof, and vegetable oils.

The effective dosage of active ingredient employed may vary depending on the particular compound employed, the mode of administration and the severity of the condition being treated. However, in general, satisfactory results are obtained when the compounds of the invention are administered at a daily dosage of from about 0.1 mg/kg to about 400 mg/kg of animal body weight, preferably given in divided doses two to four times a day, or in sustained release form. For most large mammals the total daily dosage is from about 0.07 g to 7.0 g, preferably from about 100 mg to 1000 mg. Dosage forms suitable for internal use comprise from about 100 mg to 500 mg of the active compound in intimate admixture with a solid or liquid pharmaceutically acceptable carrier. This dosage regimen may be adjusted to provide the optimal therapeutic response. For example, several divided doses may be administered daily or the dose may be proportionally reduced as indicated by the exigencies of the therapeutic situation.

The production of the above-mentioned pharmaceutical compositions and medicaments is carried out by any method known in the art, for example, by mixing the active ingredients(s) with the diluent(s) to form a pharmaceutical composition (e.g. a granulate) and then forming the composition into the medicament (e.g. tablets).

The following examples describe in detail the chemical synthesis of representative compounds of the present invention. The procedures are illustrations, and the invention should not be construed as being limited by chemical reactions and conditions they express. No attempt has been made to optimize the yields obtained in these reactions, and it would be obvious to one skilled in the art that variations in reaction times, temperatures, solvents, and/or reagents could increase the yields.

EXAMPLE 1

(5R)-3-[4-(1,3-Dihydro-1-oxo-2H-isoindol-2-yl)-3-fluorophenyl]-5-(hydroxymethyl)-2-oxazolidinone

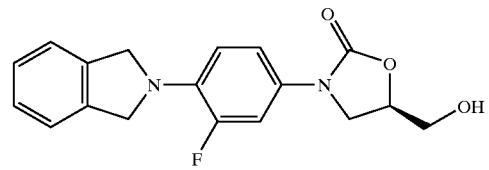

Isoindoline was synthesized employing the method of R. E. Gawley, S. R. Chemburkar, A. L. Smith, T. V. Anklekar J. Org. Chem. 1988, 53, 5381.

Step 1:

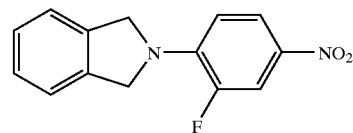

To 3,4-difluoronitrobenzene (3.02 mL, 27.3 mmols) in ethyl acetate at rt was added diisopropylethylamine (5.03 mL, 28.9 mmols) and then isoindoline (3.50 g, 29.4 mmols) and stirred overnight. A yellow precipitate (ppt) formed and was collected on a filter, washed with water and ether and dried in a vacuum oven (30° C.) to provide the product as a bright yellow solid (6.69 g, 95% yield). Mp=200–202° C. MS (M+1)=327 m/z.

Step 2:

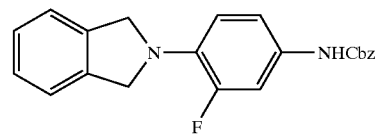

To the above nitro compound (2.62 g, 10.2 mmols) in ethanol (100 mL) was added $SnCl_2$ (9.84 g, 50.9 mmols) and was refluxed for 16 hrs. After cooling to rt the reaction mixture was added to 10% aq. NaOH (300 mL) and extracted with $CH_2Cl_2$ (6×50 mL). The combined organic washings were washed with brine (100 mL), dried over $Na_2SO_4$ and concentrated to give 2.63 g of an olive green solid (aniline), which was used without further purification. To this aniline in acetone (150 mL) and water (20 mL) was added $NaHCO_3$ (1.84 g, 21.9 mmols) and then benzylchloroformate (1.68 mL, 11.8 mmols). After stirring overnight the mixture was poured into ice water (100 mL) and the resulting tan precipitate was collected on a filter, washed with water and dried in a vacuum to give the Cbz aniline as a tan solid (3.50 g, 95% yield). Mp=146–148° C. MS (M+1)=363 m/z.

Step 3:

To the above Cbz aniline (0.74 g, 2.04 mmols) in THF (10 mL) at −78° C. was added n-BuLi (2.5 M, 0.82 mL, 2.05 mmols) dropwise. After stirring for 40 min, (R)-glycidyl butyrate (0.31 mL, 2.10 mmols) in THF (0.5 mL) was added dropwise and the resulting mixture was allowed to warm to RT overnight. A white precipitate had formed and was collected on a filter and washed with water and ether. Chromatography on silica gel with 25% ethyl acetate/hexane as eluent provided the product as a white solid (0.58 g, 87% yield). MS (M+1)=329 m/z.

EXAMPLE 2

(5R)-3-[4-(1,3-Dihydro-1-oxo-2H-isoindol-2-yl)-3-fluorophenyl]-5-[[(methylsulfonyl)oxy]methyl]-2-oxazolidinone

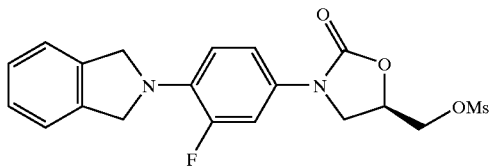

To the oxazolidinone carbinol from Example 1 (0.58 g, 1.78 mmols), in DMF (10 mL) and acetonitrile (10 mL) at 0° C. was added triethylamine (0.74 mL, 5.31 mmols) and, after 10 min, methanesulfonyl chloride (0.28 mL, 3.62 mmols). After allowing the reaction mixture to warm to RT over an hour starting material was still present so cooling and addition of triethyl amine (0.37 mL, 2.65 mmols) and methanesulfonyl chloride (0.14 mL, 1.81 mmols) was repeated. The mixture was poured into water (50 mL) and extracted with $CH_2Cl_2$ (6×20 mL), washed with brine (4×10 mL), dried over $Na_2SO_4$, concentrated to afford the crude product as a brown oil (0.95 g). MS (M+1)=407 m/z.

EXAMPLE 3

(5R)-5-(Azidomethyl)-3-[4-(1,3-dihydro-1-oxo-2H-isoindol-2-yl)-3-fluorophenyl]-2-oxazolidinone

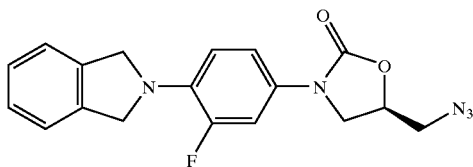

To the mesylate from Example 2 (0.95 g, 1.78 mmols) in DMF (25 mL) was added sodium azide (0.47 g, 7.23 mmols) and heated to 70° C. for 16 hrs. After cooling to rt water was added and the mixture extracted with ethyl acetate (6×25 mL), washed with brine (4×10 mL), dried over $Na_2SO_4$, concentrated to give 0.48 g of a tan solid. MS (M+1)=354 m/z.

EXAMPLE 4

N-[[(5S)-3-[4-(1,3-Dihydro-2H-isoindol-2-yl)-3-fluorophenyl]-2-oxo-5-oxazolidinyl]methyl]acetamide Compound 1

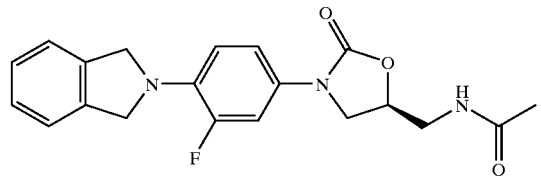

The azide from Example 3 in ethyl acetate (25 mL) was placed in a Paar flask and nitrogen bubbled through for 15 min whereupon 10% Pd/C (0.15 g, 0.14 mmol) was added. The mixture was pressurized with 50 psi of $H_2$ (g) and shaken for 16 hrs whereupon an additional amount of 10% Pd/C (0.15 g, 1.4 mmols) was added and the mixture shaken for an additional 6 hrs (at this point MS (M+1)=328 m/z). After placing the mixture under nitrogen, pyridine (0.22 mL, 2.72 mmol) and then $Ac_2O$ (0.51 mL, 5.30 mmol) were added and the mixture stirred for 2 hrs. The mixture was filtered through celite, washing with ethyl acetate (100 mL), concentrated, and chromatographed on silica (gradient elution 1%–5% $MeOH/CH_2Cl_2$) and then triturated with ethyl acetate (3×3 mL) to give 0.19 g of a white solid (Compound 1, 29% yield for 4 steps). Mp=240–242° C. MS (M+1)=370 m/z.

EXAMPLE 5

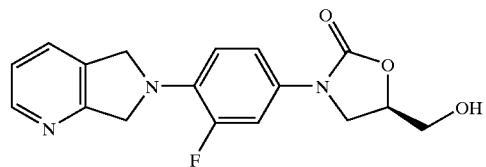

Compound 2

Step 1:

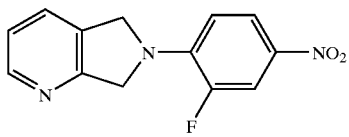

6,7-Dihydro-6-(2-fluoro-4-nitrophenyl)-5H-pyrrolo[3,4-b]pyridine: To 6,7-dihydro-5H-pyrrolo[3,4-b]pyridine dihydrochloride salt (as described by Petersen, et al. (Bayer) EP0520277A2)(42.8 g, 222 mmols) in DMF (1.2 L) was added 2,4-difluoronitrobenzene (25 mL, 224 mmols). The mixture was heated to 60° C. and DIPEA (195 mL, 1.12 mols) was added dropwise from an addition funnel over 2 hrs. After heating overnight the reaction mixture was cooled to rt, poured into water (3 L), filtered and dried in a vacuum oven (50° C.) to provide a yellow-green solid (53.8 g, 94% yield). MS (M+1)=260 m/z.

Step 2:

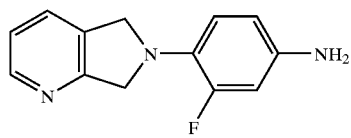

6.7-Dihydro-6-(2-fluoro-4-aminophenyl)-5H-pyrrolo[3,4-b]pyridine

To the above nitro compound (53.8 g, 208 mmol) in THF (175 mL) and methanol (600 mL) was added ammonium formate (59.0 g, 907 mmol). Nitrogen was bubbled through the reaction for approximately 30 minutes whereupon 10% Pd/C (2.20 g, 21 mmols) was added. After stirring overnight at rt under an atmosphere of nitrogen the reaction mixture was filtered through a pad of Celite, washing thoroughly with methanol (400 mL), and concentrated to a volume of ca. 200 mL. Water (300 mL) was added and the mixture extracted with ethyl acetate (5×200 mL). The combined organic layers were washed with brine, dried (Na₂SO₄), filtered, and utilized directly in the next step without further purification. MS (M+1)=230 m/z.

Step 3:

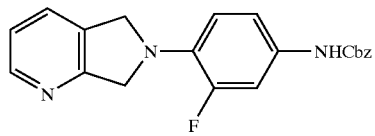

6.7-Dihydor-6-(2-fluoro-4-(Aminocarboxybenzyl)phenyl)-5H-pyrrolo[3.4-b]pyridine The above aniline (~208 mmols) in acetone (1 L) and water (160 mL) was cooled to 0° C. whereupon sodium bicarbonate (37.4 g, 445 mmols) was added followed by the dropwise addition of benzyichloroformate (34.2 mL, 228 mmols). The reaction mixture was allowed to warm to room temperature and stirred overnight whereupon a ppt formed. The reaction was poured into ice water (2 L) and the resulting precipitate was collected by filtration. The solid was washed with water and dried in a vacuum oven (50° C.) to afford the Cbz derivative (73.0 g, 97% yield) as a salmon colored powder. MS (M+1)=364 m/z.

Step 4:

(Compound 2). The above Cbz derivative (40.8 g, 112 mmols) in THF (1 L) was cooled to −78° C. under a nitrogen atmosphere. To this mixture was added n-BuLi (2.5 M, 45.8 mL, 114.5 mmols) dropwise via syringe over fifteen minutes. The reaction was warmed to room temperature and allowed to stir for 45 minutes before again being cooled to −78° C. At this point (R)-glycidyl butyrate (17.2 mL, 117 mmols) was added and the reaction mixture allowed to warm to rt overnight during which time a precipitate formed. The ppt was collected, washed with several portions of ether (5×100 mL) and dried in a vacuum oven (50° C.) to afford 40.6 g of the ether solvate of the lithium alkoxide as a tan fluffy powder. This material was then washed with several portions of water (4×200 mL) and dried in a vacuum oven (50° C.) to afford the oxazolidinone alcohol (34.1 g, 92% yield) as a tan granular solid. Mp=208–212° C., decomp. MS (M+1)=330 m/z.

EXAMPLE 6

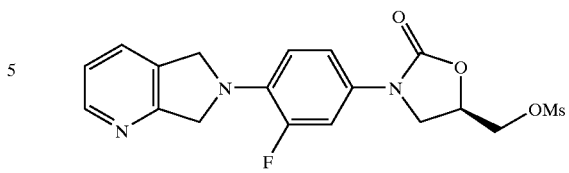

Oxazolidinone Mesylate. The above oxazolidinone carbinol (from Example 4) (33.8 g, 103 mmols) was suspended in DMF (1.25 L, previously degassed with nitrogen) at rt under a nitrogen atmosphere. Triethylamine (50 mL, 360 mmols) was added followed by the dropwise addition of methanesulfonyl chloride (13.5 mL, 174 mmols). After stirring for 3 hrs the reaction mixture was poured into water (200 mL) and methylene chloride (1 L) added. A ppt was filtered off, washed with water (3×200 mL) and dried in a vac oven (50° C.) to afford the mesylate as a tan solid (28.1 g, 67%). The organic layer was dried (Na₂SO₄), filtered and evaporated to also afford the mesylate (11.7 g, 28% yield) as a tan solid. Both where characterized with MS (M+1)=408 m/z.

EXAMPLE 7

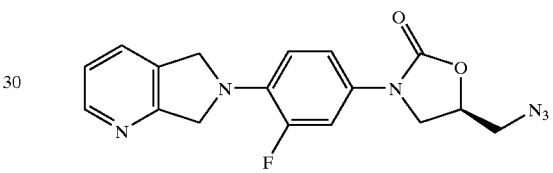

Oxazolidinone Azide. The above mesylate (from Example 5) (27.8 g, 68.2 mmols) and sodium azide (17.7 g, 271 mmols) in anhydrous DMF (1 L), previously degassed with nitrogen, were heated 95° C. for 6 hr under a nitrogen atmosphere. After cooling, the mixture was poured into stirred ice water (2 L) and formed a flocculant white ppt. The ppt was collected on a filter and washed with water (4×200 mL), dried in a vac oven (50° C.) to afford the azide as a light beige solid (22.7 g, 94% yield). Mp=175–180° C., decomp. MS (M+1)=355 m/z.

EXAMPLE 8

Compound 3

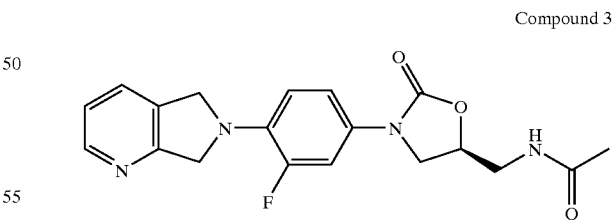

Oxazolidinone Acetamide. The above azide (from Example 6)(21.67 g, 61.16 mmol) dissolved in DMF (400 mL) and THF (500 mL) was degassed with nitrogen for 30 minutes whereupon 10% Pd/C (4.74 g, 4.4 mmols) was added and the reaction hydrogenated on a Parr apparatus (60 psi of hydrogen) for 14 hr. The reaction mixture was removed from the Parr apparatus and placed under a nitrogen atmosphere whereupon pyridine (5.44 mL, 67.3 mmols) and acetic anhydride (6.35 mL, 67.3 mmols) were added. After stirring for 1 hr the reaction mixture was filtered through a pad of Celite, washing thoroughly with methanol and then copious amounts of 50% MeOH/CH$_2$Cl$_2$ (ca. 2 L). The filtrate was evaporated to afford the crude acetamide in DMF. The mixture was slowly added to water (2 L) and the ppt collected on a filter, washed with water (5×400 mL) and dried in a vac oven (50° C.) to provide the acetamide as an analytically pure white solid (14.2 g, 63% yield). The combined filtrates were extracted with methylene chloride (5×200 mL), dried over Na$_2$SO$_4$ and concentrated. Water was added to the residue and the resulting ppt was filtered off and dried in a vac oven (50° C.) to afford a second crop of the acetamide as a light tan, fluffy solid (5.61 g, 25%). For the analytically pure material Mp=229–230° C., decomp. MS (M+1)=371 m/z.

EXAMPLE 9

Compound 4

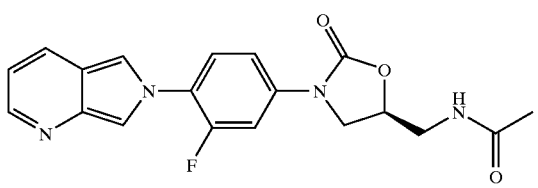

The above acetamide from Example 8 (2.51 g, 6.78 mmols) was taken up in CH$_2$Cl$_2$ and MnO$_2$ added (23.9 g, 234 mmols). After stirring overnight the reaction mixture was filtered through celite, concentrated and chromatography on silica with 10% MeOH/CH$_2$Cl$_2$ as eluent to afford the product as a light yellow solid (0.48 g, 19% yield). Mp=220–225° C. decomp. MS (M+1)=369 m/z.

EXAMPLE 10

Compound 5

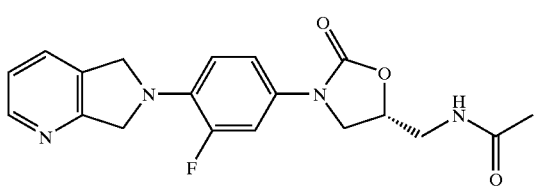

Compound 5 was prepared as in Example 8 except (S)-glycidyl butyrate was employed in the oxazolidinone formation. The product was isolated as a light tan solid. Mp=227–230° C. decomp. MS (M+1)=371 m/z.

EXAMPLE 11

Compound 6

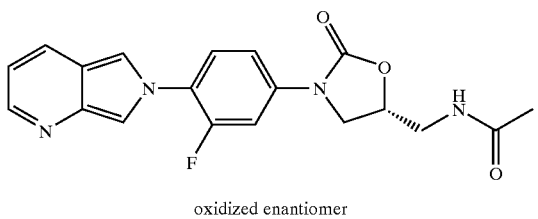

oxidized enantiomer

Compound 6 was prepared as in Example 9 and isolated as a light yellow solid. Mp=181–185° C. decomp. MS (M+1)=369 m/z.

EXAMPLE 12

Compound 7

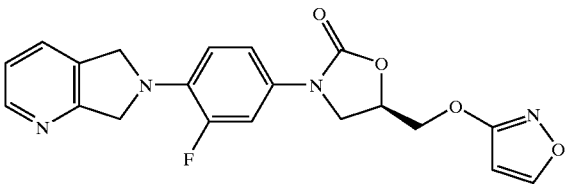

To 5-hydroxyisoxazole (prepared as in *Chem Pharm Bull* 1966, 14(11), 1277) (0.174 g, 2.04 mmols) in DMF was added NaH (60% in oil)(0.105 g, 2.62 mmols). After stirring for 30 min the mesylate (from Example 6) (0.744g, 1.82 mmols) was added in one portion and the mixture stirred at 60° C. overnight. After cooling to rt water was added and a ppt was collected on a filter, air dried and chromatographed on silica with 2.5% MeOH/CH$_2$Cl$_2$ as eluent to afford the product as a white solid (0.140 g, 19% yield). Mp=182–185° C. MS (M+1)=397 m/z.

EXAMPLE 13

Compound 8

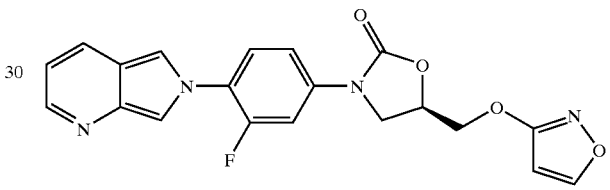

To the above oxazolidinone (from Example 12) (0.264 g, 6.66 mmols) was taken up in CH$_2$Cl$_2$ and MnO$_2$ added (1.66 g, 16.2 mmols) in two portions over two days. After stirring for two days the reaction mixture was filtered through celite, concentrated and chromatographed on silica with 10% MeOH/CH$_2$Cl$_2$ as eluent to afford the product as a light yellow solid (0.086 g, 32% yield). Mp=133–135° C. MS (M+1)=395 m/z.

EXAMPLE 14

Compound 9

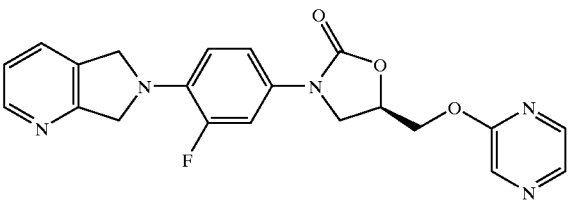

To NaH (60% by wt in oil)(0.03 g, 0.76 mmol) in DMF (5 mL) was added oxazolidinone carbinol (from Example 5) (0.23 g, 0.71 mmol) in four portions. After stirring for 30 min 2-chloropyrazine (0.065 mL, 0.71 mmol) was added via syringe and stirred overnight at rt. Water was added and a ppt was collected on a filter, air dried and chromatographed on silica with 5% MeOH/CH$_2$Cl$_2$ as eluent to afford the product as a white solid (0.067 g, 23% yield). Mp=225–230° C. MS (M+1)=408 m/z.

EXAMPLE 15

Compound 10

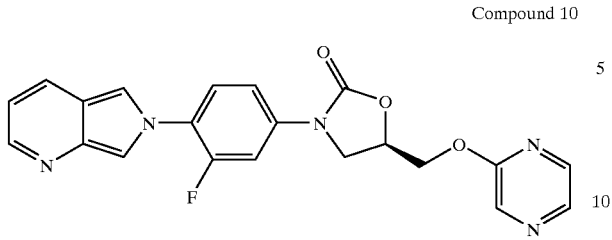

The above oxazolidinone (from Example 14) (0.024 g, 0.058 mmol) in $CH_2Cl_2$ (5 mL) was added $MnO_2$ (0.07 g, 0.7 mmol). After stirring overnight the reaction mixture was filtered through Celite and concentrated to afford the product as a very light yellow solid (0.015 g, 64% yield). Mp=192–194° C. MS (M+1)=406 m/z.

EXAMPLE 16

Compound 11

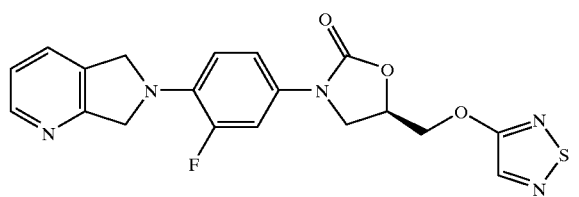

To a suspension of the oxazolidinone carbinol (prepared in Example 5) (330 mg, 1.0 mmol), triphenylphosphine (260 mg, 1.1 mmols) and 4-hydroxy-1,2,5-thiadiazole (100 mg, 1.0 mmol) (as prepared in U.S. Pat. No. 3,391,150 [7/2/68]) in THF (8 mL) was added diisopropylazodicarboxylate (0.20 mL, 1.1 mmols). After stirring overnight at rt the reaction mixture was filtered, washed with methanol, and air dried to afford a yellow crystalline solid (60 mg, 15% yield). Mp=185–187° C. MS (M+1)=414 m/z.

EXAMPLE 17

Compound 12

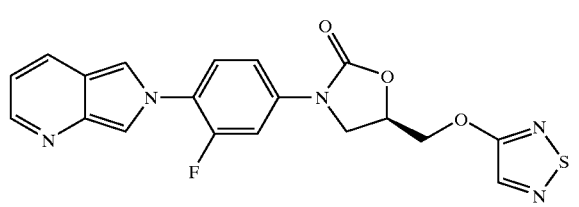

To the oxazolidinone (prepared in Example 16) (160 mg, 0.39 mmol) suspended in $CH_2Cl_2$ (1.0 mL) was added $MnO_2$ (four additions of 150 mg over four days). The reaction mixture was filtered through a plug of Celite, washed with $CH_2Cl_2$ (15 mL), and concentrated under reduced pressure to afford the product as a white crystalline solid (63 mg, 40% yield). Mp=185–188° C. MS (M+1)=412 m/z.

EXAMPLE 18

Compound 13

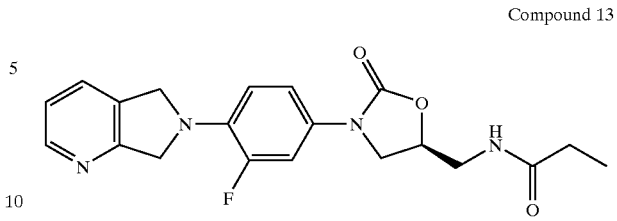

To the amine (as prepared in Example 8) (100 mg, 0.30 mmol) and potassium carbonate (100 mg, 0.72 mmol) suspended in methanol (1.0 mL), was added propionyl chloride (50 mg, 0.54 mmol). After stirring overnight at 80° C. the reaction mixture was cooled and water was added. A precipitate was filtered off, washed with methanol and air dried to afford the product as a brown crystalline solid (15 mg, 13% yield). Mp=110–112° C. MS (M+1)=385 m/z.

EXAMPLE 19

Compound 14

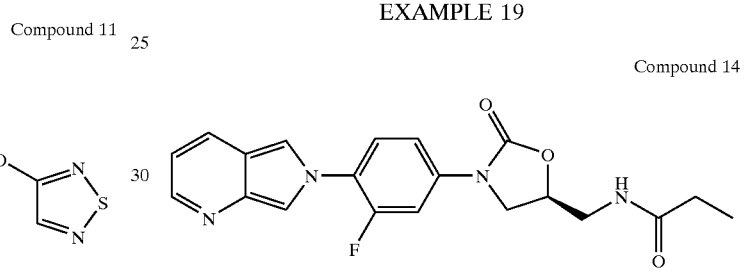

To the amide (prepared in Example 18) (15 mg, 0.04 mmol) suspended in $CH_2Cl_2$ (1.0 mL), was added $MnO_2$ (200 mg) at rt. After stirring overnight, the reaction mixture was filtered through a plug of Celite, washed with $CH_2Cl_2$ (10 mL), and concentrated under reduced pressure to afford the product as an light brown crystalline solid (1.6 mg, 8% yield). MS (M+1)=383 m/z.

EXAMPLE 20

Compound 15

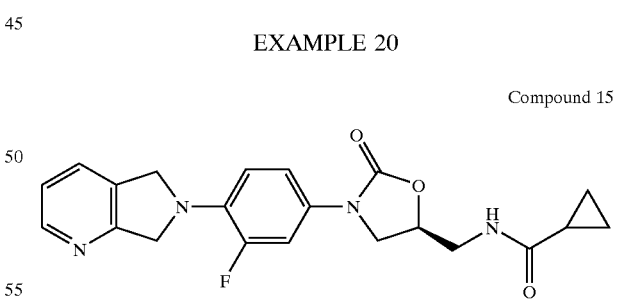

To the amine (as prepared in Example 8) (60 mg, 0.18 mmol) and potassium acetate (60 mg, 0.61 mmol) suspended in methanol (1.0 mL), was added cyclopropyl carbonyl chloride (120 mg, 1.15 mmols). After stirring at rt overnight, the reaction mixture was filtered, rinsed with methanol, and then concentrated to dryness under reduced pressure. The resulting solid residue was triturated with water and filtered to afford the product as a brown crystalline solid (36 mg, 50% yield). Mp=235–240° C. MS (M+1)=397 m/z.

EXAMPLE 21

Compound 16

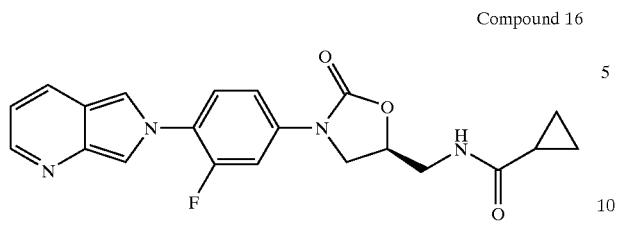

To the amide (prepared in Example 20) (36 mg, 0.09 mmol) suspended in $CH_2Cl_2$ (1.0 mL), was added $MnO_2$ (three portions of 100 mg over three days) at rt. The reaction mixture was filtered through a plug of Celite, washed with $CH_2Cl_2$ (10 mL), and concentrated under reduced pressure to afford the product as an off-white crystalline solid (3 mg, 8% yield). MS (M+1)=395 m/z.

EXAMPLE 22

Compound 17

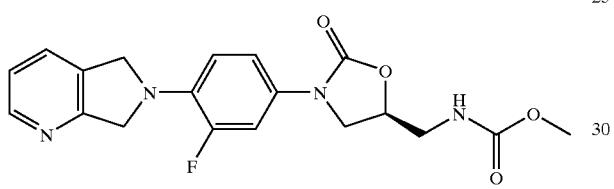

To the amine (prepared in Example 8) (60 mg, 0.18 mmol) and potassium acetate (60 mg, 0.61 mmol) suspended in methanol (1.0 mL), was added dropwise methyl chloroformate (120 mg, 1.27 mmols). After stirring for four hours at rt, the reaction mixture was filtered, diluted with water, and concentrated under reduced pressure to remove the methanol. The aqueous solution was extracted with ethyl acetate (5×5 mL). The combined organics were washed with water, dried over $MgSO_4$, filtered, and concentrated to provide an oil which was triturated with ether to afford a brown crystalline solid (35 mg, 50% yield). MS (M+1)=387 m/z.

EXAMPLE 23

Compound 18

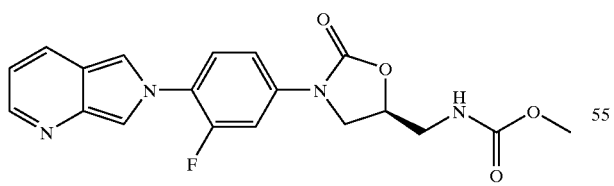

To the carbamate (prepared in Example 22) (33 mg, 0.08 mmol) suspended in $CH_2Cl_2$ (1.0 mL), was added $MnO_2$ (150 mg). After stirring overnight at rt the reaction mixture was filtered through a plug of Celite, washed with $CH_2Cl_2$ (10 mL), and concentrated under reduced pressure to afford the product as a yellow crystalline solid (6.0 mg, 18% yield). MS (M+1)=385 m/z.

EXAMPLE 24

Compound 19

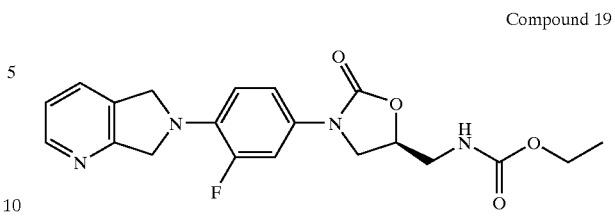

To the amine (prepared in Example 8) (60 mg, 0.18 mmol) and potassium acetate (60 mg, 0.61 mmol) suspended in methanol (1.0 mL) was added dropwise ethyl chloroformate (0.1 mL, 1.04 mmols). After stirring overnight at rt the reaction mixture was filtered, diluted with water, and concentrated under reduced pressure to remove the methanol. The aqueous solution was extracted with ethyl acetate (5×5 mL). The combined organics were washed with water, dried over $MgSO_4$, filtered, and concentrated. The resulting semi-solid was treated with water, filtered and air-dried to afford a brown crystalline solid (18 mg, 30% yield). MS (M+1)= 401 m/z.

EXAMPLE 25

Compound 20

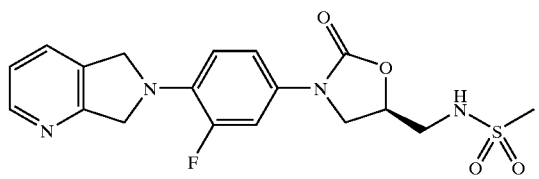

To the amine (prepared in Example 8) (95 mg, 0.29 mmol) suspended in pyridine (0.5 mL) was added methane sulfonylchloride (0.08 mL, 1.0 mmol). After stirring overnight at rt the pyridine was removed under a stream of nitrogen. The residue was treated with water, filtered and air-dried to afford a brown solid (45 mg, 38% yield). Mp=172–176° C. MS (M+1)=407 m/z.

EXAMPLE 26

Compound 21

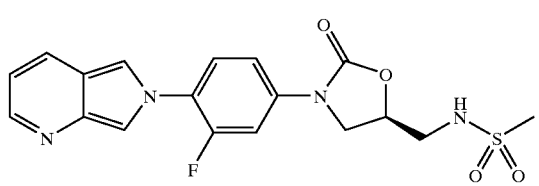

To the sulfonamide (prepared in Example 25) (10 mg, 0.02 mmol) suspended in $CH_2Cl_2$ (1.0 mL), was added $MnO_2$ (100 mg, 10 mmols). After stirring overnight the reaction mixture was filtered through a plug of Celite, washed with $CH_2Cl_2$ (10 mL), and concentrated under reduced pressure to afford the product as a brown crystalline solid (0.5 mg, 5% yield). MS (M+1)=405 m/z.

EXAMPLE 27

Compound 22

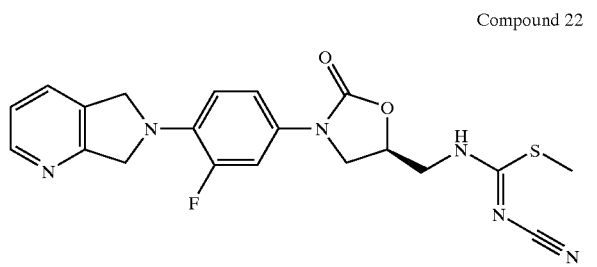

To the amine (prepared in Example 8) (200 mg, 0.61 mmol) suspended in toluene (8 mL), was added dimethyl-N-cyanodithioiminocarbonate (89 mg, 0.61 mmol). After stirring overnight at reflux the toluene was decanted and the oily residue treated with methanol, filtered, and air-dried to afford a brown crystalline solid (62 mg, 20% yield). Mp=204–207° C. MS (M+1)=427 m/z.

EXAMPLE 28

Compound 23

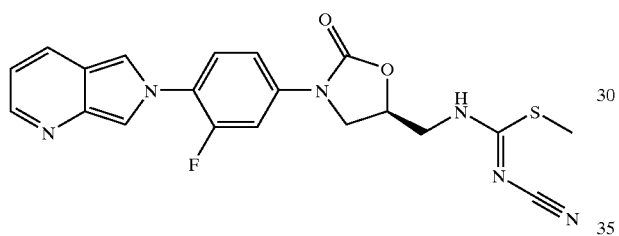

A suspension of the thioimidate (from Example 27) (45 mg, 0.10 mmol) and MnO$_2$ (200 mg, 2.0 mmols) in CH$_2$Cl$_2$ were stirred at rt for one day whereupon a second addition of MnO$_2$ (150 mg, 1.5 mmols) was added. After an additional day of stirring the mixture was filtered through Celite, washed with CH$_2$Cl$_2$ (10 mL), concentrated to afford a yellow crystalline solid (20 mg, 45% yield). MS (M+1)=426 m/z.

EXAMPLE 29

Compound 24

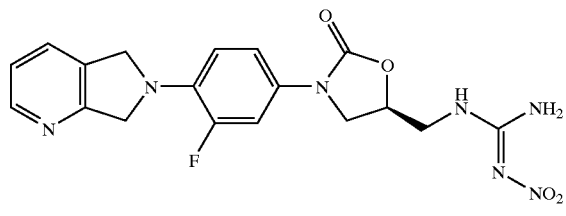

A suspension of the amine (prepared in Example 8) (165 mg, 0.5 mmol) and 2-methyl-1-nitro-2-thiopseudourea (94 mg, 0.70 mmol) (as prepared as in EP 0539204/ 1993) in methanol (2 mL) was refluxed for four hours. After cooling to rt the reaction mixture was filtered and air dried to afford a yellow crystalline solid (50 mg, 24% yield). Mp=202–206° C. MS (M+1)=416 m/z.

EXAMPLE 30

Compound 25

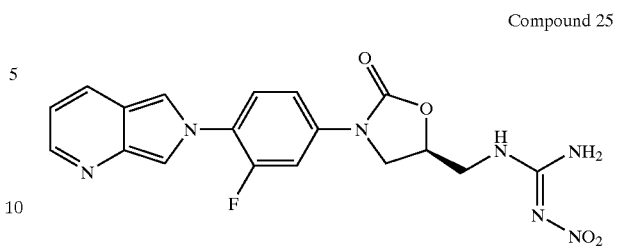

To the nitroguanidine (prepared in Example 29) (35 mg, 0.08 mmol) suspended in CH$_2$Cl$_2$ (1.0 mL) was added MnO$_2$ (three additions of 100 mg over three days). The reaction mixture was filtered through a plug of Celite, washed with CH$_2$Cl$_2$ (10 mL), and concentrated under reduced pressure to afford the product as a yellow crystalline solid (1.6 mg, 4% yield). MS (M+1)=414 m/z.

EXAMPLE 31

Compound 26

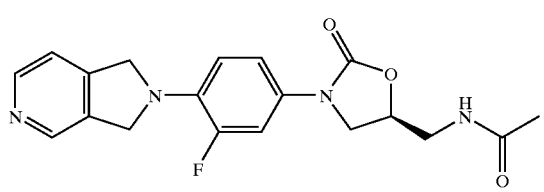

The starting material 6,7-dihydro-5H-pyrrolo[3,4-c] pyridine was prepared as in U.S. Pat. No. 5,371,090 to Petersen et al. Compound 26 was then prepared as in Example 8 except the acetamide was recrystallized from acetonitrile to give a light tan solid. Mp=182–190° C. decomposition. MS (M+1)=371 m/z.

EXAMPLE 32

Compound 27

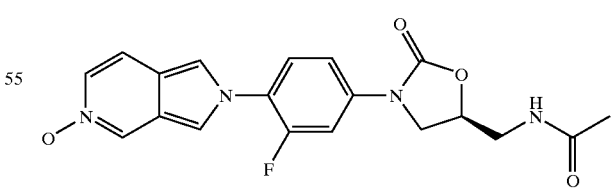

Compound 27 was isolated from the final step of Example 31 via chromatography (5% MeOH/CH$_2$Cl$_2$ as eluent) of the mother liquors collected from recrystallization. Light yellow solid, Mp=219–225° C. decomp. MS (M+1)=385 m/z.

EXAMPLE 33

Compound 28

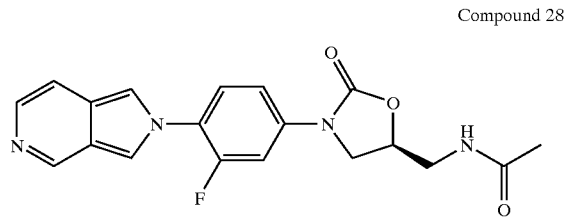

Compound 28 was prepared as in Example 9 except with 10% MeOH/CH$_2$Cl$_2$ as eluent. Light yellow solid, Mp=219–225° C. decomposition. MS (M+1)=369 m/z.

EXAMPLE 34

Compound 29

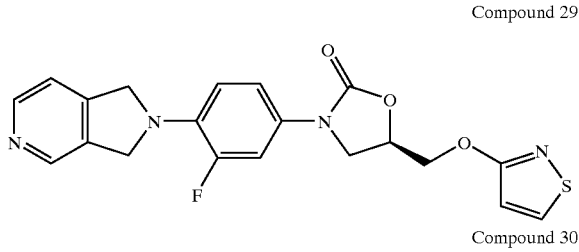

Compound 30

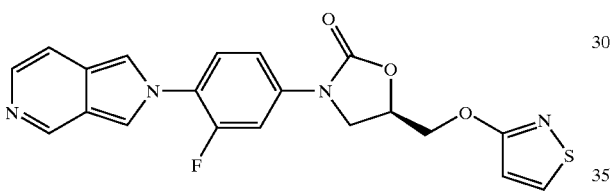

Isothiazole (0.088 g, 0.87 mmol)(prepared as in *J Heterocyclic Chem* 1971, 8, 591) was added portionwise at rt to a suspension of sodium hydride (0.036 g, 0.91 mmol, 60% in oil) in DMF (4 mL) under nitrogen. The mixture was stirred for 30 minutes whereupon the mesylate from Example 31 (0.31 g, 0.76 mmol), in DMF (10 mL), was added all at once. After stirring for 6 hours at 60° C. the reaction mixture was cooled to rt, diluted with water (50 mL), and extracted with ethyl acetate (3×50 mL). The combined organics were washed several times with water, then once with brine, dried over sodium sulfate, concentrated, and chromatographed on silica with 5% MeOH/EtOAc as eluent. Two products were isolated from the chromatography: 0.050 g of Compound 29; and 0.022 g of Compound 30. Overall yield, 30%.

Compound 29 MS (M+1)=413.0

Compound 30 MS (M+1)=411.1

EXAMPLE 35

Compound 31

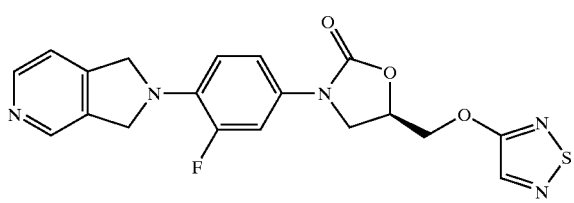

Compound 32

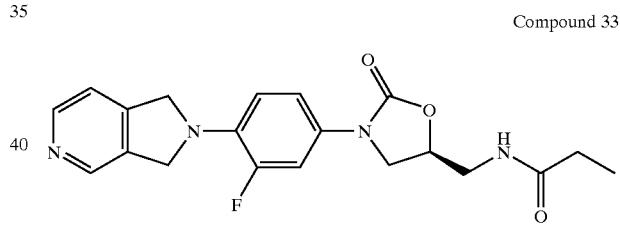

To a suspension of sodium hydride (0.036 g, 0.91 mmol, 60% in oil) in DMF (4 mL) at rt under nitrogen was added portion wise 4-hydroxy-1,2,5-thiadiazole (0.088 g, 0.87 mmol) (as prepared in U.S. Pat. No. 3,391,150 [7/2/68]). After stirring for 30 min the mesylate from Example 31 (0.310 g, 0.76 mmol), in DMF (10 mL), was added all at once. After stirring for 6 hours at 60° C. the reaction mixture was cooled to rt, diluted with water (50 mL), and extracted with ethyl acetate (3×50 mL). The combined organics were washed several times with water, then once with brine, dried over sodium sulfate, concentrated, and chromatographed on silica with 2% MeOH/EtOAc as eluent. Two products were isolated from the chromatography: 0.035 g of Compound 31; and 0.0093 g of Compound 32. Overall yield, 14%.

Compound 31 MS (M+1)=414.0

Compound 32 MS (M+1)=412.1

EXAMPLE 36

Compound 33

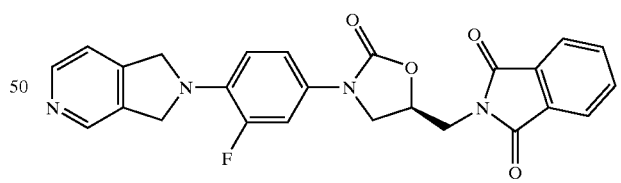

Step 1:

To the mesylate from Example 31 (2.45 g, 6.01 mmol) dissolved in degassed DMF (100 mL) under nitrogen was added potassium phthalimide (2.23 g, 12.0 mmols). After heating at 65° C. for 3 hours the reaction mixture was cooled, poured into water (300 mL), and extracted with methylene chloride (3×200 mL). The combined organics were washed with water (3×150 mL) dried over sodium sulfate, concentrated to a tan solid. This solid was washed with water and dried in a high vacuum oven at 50° C. to afford 2.20 g (80%) of the oxazolidinone phthalimide. MS=459.1 (M+1).

Step 2:

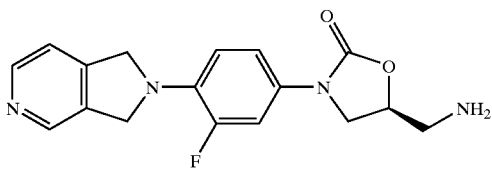

To the above phthalimide (0.97 g, 2.1 mmols) in degassed methanol (30 mL) under nitrogen was added hydrazine monohydrate (0.2 mL, 4.3 mmols) dropwise. After refluxing for 12 hours the reaction mixture was cooled to rt, and concentrated, suspended $CH_2Cl_2$ and filtered. The crude oxazolidinone amine was concentrated and used without further purification.

Step 3:
Compound 33,

To the crude amine (0.14 g, 0.44 mmol) in $CH_2Cl_2$ (5 mL) was added pyridine (0.14 mL, 18 mmols) followed by propionyl chloride (0.76 mL, 0.88 mmol). After stirring for 5 hrs at rt the solution was poured into water (20 mL) and extracted with methylene chloride (3×10 mL). The combined extracts were washed with water (10 mL) and 1 M NaOH (aq) (10 mL), dried over sodium sulfate, concentrated and chromatographed using neat EtOAc as eluent to afford the propionyl amide as a gold oil (0.020 g, 12% yield). MS=385.2 (M+1).

EXAMPLE 37

Compound 34

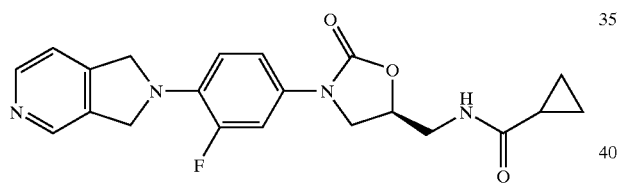

To the crude amine (as prepared in Example 36) (0.144 g, 0.437 mmol) in methylene chloride (5 mL) was added pyridine (0.14 mL, 1.7 mmols), followed by cyclopropane carbonyl chloride (0.08 mL, 0.88 mmol). After stirring for 5 hrs at rt the solution was poured into water (20 mL) and extracted with methylene chloride (3×10 mL). The combined extracts were washed with water (10 mL) and 1 M NaOH (aq) (10 mL), dried over sodium sulfate, concentrated and chromatographed using a gradient elution of 1% to 5% to 10% MeOH/EtOAc. The desired product eluted with 5% MeOH/EtOAc and was concentration to afford the product as a white powder (0.012 g, 7% yield). MS=397.2 (M+1).

EXAMPLE 38

Compound 35

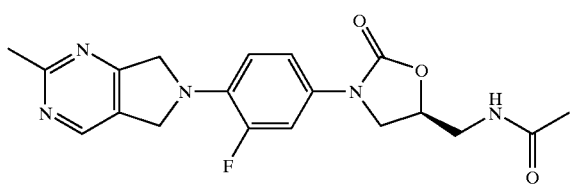

Step 1:

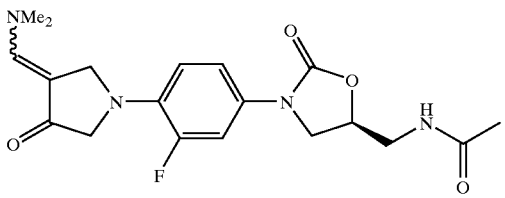

To N-[(3-pyrrolidinone-3-fluorophenyl) 5-oxazolidinyl] methyl acetamide (prepared according to WO96/13502) (0.150 g, 0.447 mmols) was added methoxy-bis (dimethylamino)methane (1 mL). After heating at 50° C. for 15 min the reaction mixture was concentrated to provide the crude β-ketoenamine which was used without further purification.

Step 2;

Compound 35

To ethanolic NaOEt (made from 0.027 g Na in 3 mL EtOH) was added acetamidine hydrochloride (0.113 g, 1.19 mmols) and the above β-ketoenamine oxazolidinone acetamide. After refluxing for 3 hrs the reaction mixture was cooled to rt, concentrated, taken up in chloroform, and washed with water (3×8 mL). After drying over sodium sulfate the crude product was concentrated, dissolved in 5% MeOH/EtOAc, and filtered to afford the product as an off-white solid (0.052 g, 45% yield). Mp=234° C., decomp. MS=385.9 (M+1).

EXAMPLE 39

Compound 36

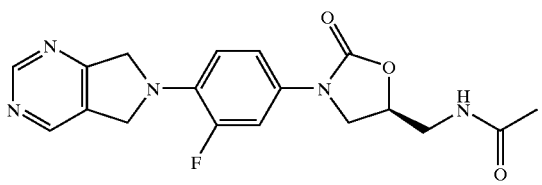

To N-[(3-pyrrolidinone-3-fluorophenyl) 5-oxazolidinyl] methyl acetamide (prepared according to WO96/13502) (0.099 g, 0.29 mmol) was added methoxy-bis (dimethylamino)methane (1.0 mL). After heating at 50° C. for 2 hrs the reaction mixture was concentrated to provide the crude β-ketoenamine. To this mixture was added benzene (5 mL), DMF (1 mL) and formamidine acetate (0.55 g, 5.3 mmols). After heating overnight at 95° C. the reaction mixture was cooled to rt and water (8 mL) was added. A ppt formed and was collected by filtration, dried in a vacuum oven (50° C.), and chromatographed on silica with 5% MeOH/$CH_2Cl_2$ as eluent to afford the product as a white powder (0.037 g, 34% yield). Mp=230–232° C. MS (M+1)= 372 m/z.

EXAMPLE 40

Compound 37

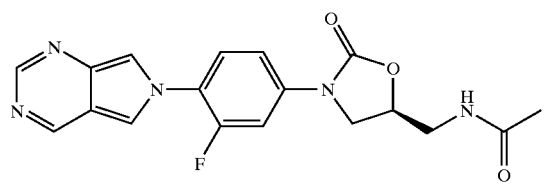

The above acetamide from Example 39 (0.020 mg, 0.054 mmol) was taken up in $CH_2Cl_2$ (5 mL) and $MnO_2$ added (0.10 g, 0.98 mmol). After stirring overnight at rt the reaction mixture was filtered through Celite and concentrated to afford the product as a light yellow solid (0.016 g, 80% yield). Mp=164–166° C. MS (M+1)=370 m/z.

EXAMPLE 41

Compound 38

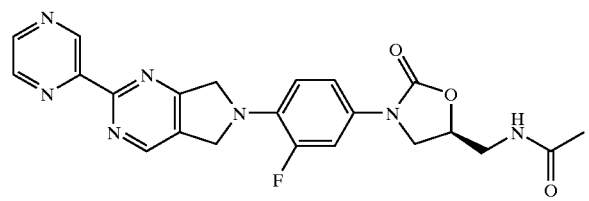

To the β-ketoenamine (prepared as in Example 39) was added benzene (5 mL), DMF (1 mL) and pyrazine-2-carboxamidine hydrochloride (0.62 g, 3.9 mmols). After heating overnight at 95° C. the reaction mixture was cooled to rt and water (8 mL) was added. A ppt formed and was collected by filtration, dried in a vacuum oven (50° C.), and chromatographed on silica with 5% $MeOH/CH_2Cl_2$ as eluent to afford the product as a light yellow solid (0.0026 g, 2% yield). Mp=212–214° C. MS (M+1)=450 m/z.

EXAMPLE 42

Compound 39

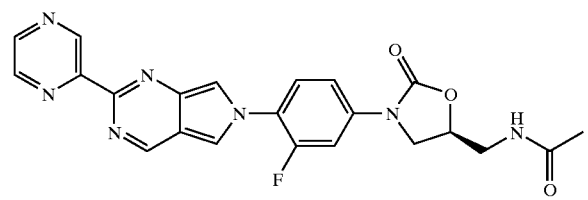

The above acetamide from Example 39 (0.040 g, 0.088 mmols) was taken up in $CH_2Cl_2$ (10 mL) and $MnO_2$ (0.36 g, 3.5 mmols) added in three portions over three days. After stirring for three days the reaction mixture was filtered through Celite, concentrated and chromatography on silica with 7% $MeOH/CH_2Cl_2$ as eluent. Two products were isolated from the chromatography: 0.001 g of Compound 39 as a light yellow solid (4% yield); and 0.002 g of Compound 40 as a yellow solid (4% yield).

Compound 39: MS (M+1)=448 m/z.
Compound 40: MS (M+1)=464 m/z.

EXAMPLE 43

Compound 41

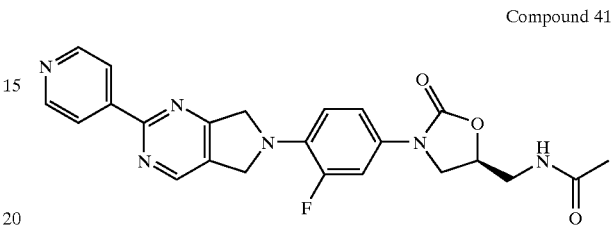

To the β-ketoenamine (prepared as in Example 39) was added benzene (5 mL), DMF (1 mL) and 4-amidinopyridine hydrochloride (0.81 g, 5.2 mmols). After heating overnight at 95° C. the reaction mixture was cooled to rt and water (8 mL) was added. A ppt formed and was collected by filtration, dried in a vacuum oven (50° C.), and chromatographed on silica with 5% $MeOH/CH_2Cl_2$ as eluent to afford the product as a light yellow solid (0.072 g, 55% yield). Mp=245–250° C., decomp. MS (M+1)=449 m/z.

EXAMPLE 44

Compound 42

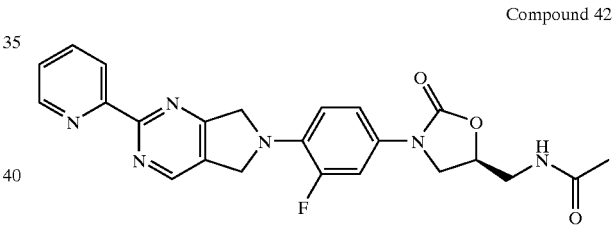

To the β-ketoenamine (prepared as in Example 39) was added benzene (5 mL), DMF (1 mL) and 2-amidinopyridine hydrochloride (0.61 g, 3.9 mmols). After heating overnight at 95° C. the reaction mixture was cooled to rt and water (8 mL) was added. A ppt formed and was collected by filtration, dried in a vacuum oven (50° C.), and chromatographed on silica with 5% $MeOH/CH_2Cl_2$ as eluent to afford the product as a yellow powder (0.054 g, 40% yield). Mp=216–220° C. MS (M+1)=449 m/z.

EXAMPLE 45

Compound 43

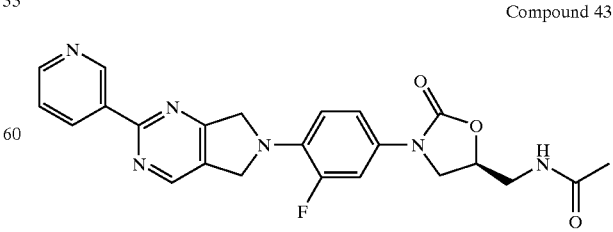

To the β-ketoenamine (prepared as in Example 39) was added benzene (5 mL), DMF (2 mL) and 3-amidinopyridine hydrochloride (0.49 g, 3.1 mmols). After heating overnight at 95° C. the reaction mixture was cooled to rt and water (8 mL) was added. A ppt formed and was collected by filtration, dried in a vacuum oven (50° C.), and chromatographed on silica with 5% MeOH/CH$_2$Cl$_2$ as eluent to afford the product as a light purple, crystalline solid (0.044 g, 33% yield). Mp=265–270° C., decomp. MS (M+1)=449 m/z.

EXAMPLE 46

Compound 44

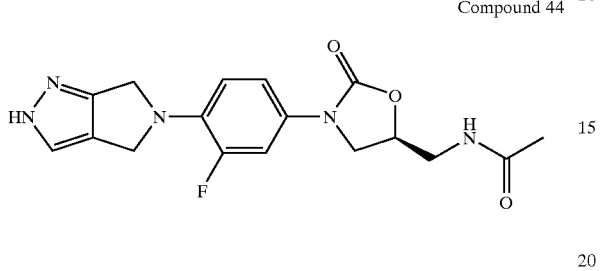

To the β-ketoenamine (prepared as in Example 39) was added benzene (5 mL), DMF (2 mL) and hydrazine hydrochloride (0.22 g, 3.2 mmols). After heating overnight at 95° C. the reaction mixture was cooled to rt and water (8 mL) was added. A ppt formed and was collected by filtration, dried in a vacuum oven (50° C.), and chromatographed on silica with 5% MeOH/CH$_2$Cl$_2$ as eluent to afford the product as off-white powder (0.022 g, 21% yield). Mp=244–247° C., decomp. MS (M+1)=360 m/z.

EXAMPLE 47

Compound 45

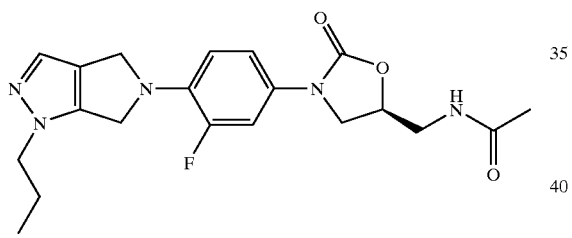

To the β-ketoenamine (prepared as in Example 39) was added benzene (5 mL), DMF (2 mL) and n-propylhydrazine oxalate (0.87 g, 5.3 mmols). After heating overnight at 95° C. the reaction mixture was cooled to rt and water (8 mL) was added. A ppt formed and was collected by filtration, dried in a vacuum oven (50° C.), and chromatographed on silica with 5% MeOH/CH$_2$Cl$_2$ as eluent to afford the product as a light yellow solid (0.081 g, 55% yield). Mp=204–208° C. MS (M+1)=402 m/z.

EXAMPLE 48

Compound 46

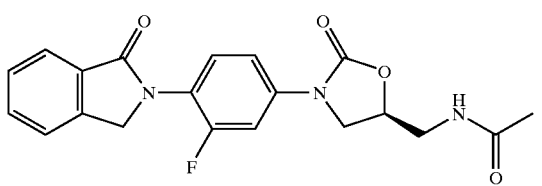

The starting material aniline (N-[[(5S)-3-(4-amino-3-fluorophenyl)-2-oxo-5-oxazolidinyl]methyl]-acetamide) was prepared as in World Patent WO 96/23788. To phthalic dicarboxaldehyde (0.0522 g, 0.378 mmol) in acetonitrile (1 mL) was added glacial acetic acid (0.05 mL, 0.87 mmol) and then the above aniline (0.0955 g, 0.357 mmol) in acetonitrile (5 mL) dropwise. After 4 hrs water (10 mL) was added and a precipitate was collected on a filter and washed with water and ether to provide Compound 46 as a light green solid (0.0655 g, 48%). Mp=211–214° C. MS (M+1)=384 m/z.

EXAMPLE 49

Compound 47

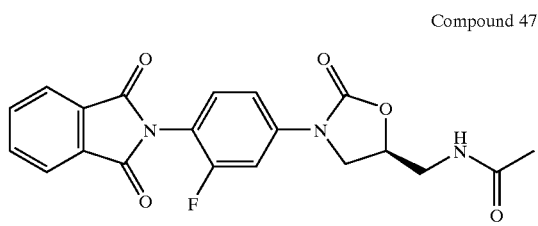

To starting material aniline (N-[[(5S)-3-(4-amino-3-fluorophenyl)-2-oxo-5-oxazolidinyl]methyl]-acetamide) (0.095 g, 0.36 mmol)(as prepared in World Patent WO 96/23788) in CH$_2$Cl$_2$ (5 mL) was added triethylamine (0.15 mL, 1.1 mmols) and phthaloyl dichloride (0.056 mL, 0.39 mmol). After stirring overnight a solid was collected on a filter, washed with water (10 mL) and dried in vacuum oven (50° C.) to afford the product as a off-white solid (0.060, 42%). Mp=240–242° C. MS (M+1)=398 m/z.

EXAMPLE 50

Compound 48

Compound 49

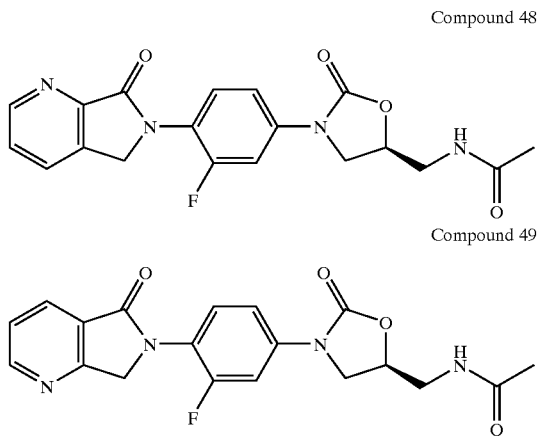

To starting material aniline (N-[[(5S)-3-(4-amino-3-fluorophenyl)-2-oxo-5-oxazolidinyl]methyl]-acetamide) (0.20 g, 0.75 mmol)(as prepared in World Patent WO 96/23788) in acetonitrile (5 mL) was added 2,3-pyridine dicarboxaldehyde (0.10 g, 6.6 mmols) and glacial acetic acid (0.050 mL, 0.87 mmol). After stirring for 5 hrs the reaction mixture was concentrated and chromatographed on silica with 2.5% MeOH/CH$_2$Cl$_2$ as eluent to afford the two products: 0.035 g of Compound 52 (12%) as a yellow solid; and 0.011 g of Compound 53 (4%) as a yellow solid.

Compound 48: Mp=230–232° C. MS (M+1)=385 m/z.

Compound 49: Mp=207–209° C. MS (M+1)=385 m/z.

EXAMPLE 51

Compound 50

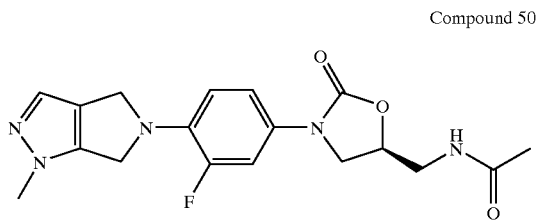

To the crude β-ketoenamine from Example 38 (~0.276 mmol) was added benzene (5 mL), DMF (2 mL), methylhydrazine (0.15 mL, 2.8 mmols) and HCl in ether (2.75 mL, 1.0 M). After heating overnight at 90° C. the reaction mixture was cooled to rt and water (8 mL) was added. A ppt formed and was collected on a filter, dried in a vacuum oven (50° C.), and chromatographed on silica with 10% MeOH/CH$_2$Cl$_2$ as eluent to afford the product as a light yellow solid (0.0285 g, 28% yield). Mp=211–213° C. MS (M+1)=374 m/z.

EXAMPLE 52

Compound 51

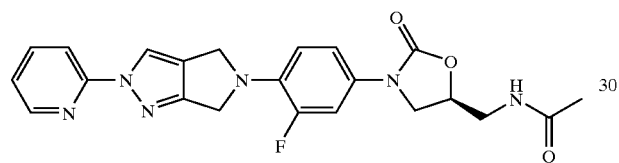

To the crude β-ketoenamine from Example 38 (0.282 mmol) was added benzene (3 mL), DMF (2 mL), 2-hydrazinopyridine (0.3214 g, 2.8 mmols) and HCl in ether (2.85 mL, 1.0 M). After heating overnight at 90° C. the reaction mixture was cooled to rt and water (8 mL) was added. A ppt formed and was collected on a filter, dried in a vacuum oven (50° C.), and chromatographed on silica with 10% MeOH/CH$_2$Cl$_2$ as eluent to afford the product as a tan solid (0.0046 g, 4% yield). Mp=259–261° C., decomp. MS (M+1)=437 m/z.

EXAMPLE 53

Compound 52

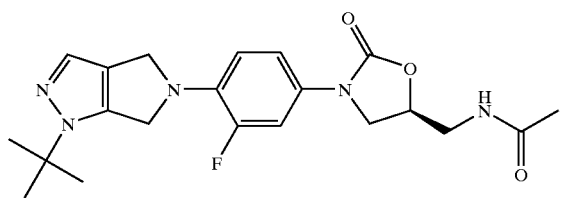

To the crude β-ketoenamine from Example 38 (0.2481 mmol) was added benzene (3 mL), DMF (2 mL), and tert-butylhydrazine hydrochloride (0.3090 g, 2.48 mmols). After heating overnight at 90° C. the reaction mixture was cooled to RT and water (8 mL) was added. A ppt formed and was collected on a filter, dried in a vacuum oven (50° C.), and triturated with 10% MeOH/CH$_2$Cl$_2$ to afford the product as a light yellow glassy solid (0.0570 g, 55% yield). Mp=155–157° C. MS (M+1)=416 m/z.

EXAMPLE 54

Compound 53

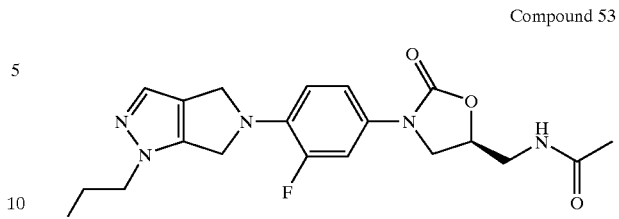

To the crude β-ketoenamine from Example 38 (~0.298 mmol) was added benzene (3 mL), DMF (2 mL), 2-hydroxyethylhydrazine (0.23 mL, 3.4 mmols) and HCl in ether (3.00 mL, 1.0 M). After heating overnight at 90° C. the reaction mixture was cooled to RT and water (8 mL) was added. A ppt formed and was collected on a filter, dried in a vacuum oven (50° C.), and chromatographed on silica with 10% MeOH/CH$_2$Cl$_2$ as eluent to afford the product as a light yellow solid (0.0517 g, 43% yield). Mp=163–165° C. MS (M+1)=404 m/z.

EXAMPLE 55

Compound 54

Compound 55

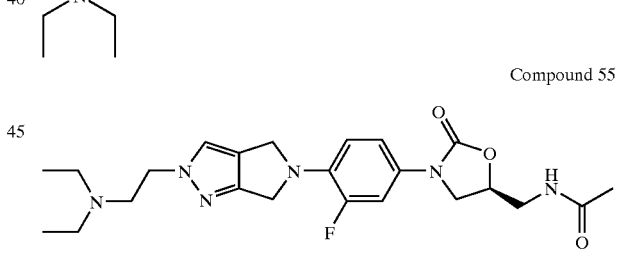

To Compound 44 (0.0481 g, 0.134 mmol) in DMF at RT was added sodium hydride (60% in oil)(0.008 g, 0.2 mmol) and the mixture stirred for 20 min. To this mixture was added 2-(diethylamino)ethyl chloride (0.16 mL, 1.0 M in benzene) and the mixture was stirred at 40° C. overnight. The mixture was treated with sat. aqueous NH$_4$Cl (10 mL) and water (5 mL). The mixture was extracted with EtOAc (10×20 mL), dried over Na$_2$SO$_4$, concentrated and chromatographed on silica with 10% MeOH/CH$_2$Cl$_2$ as eluent to afford the two products. The isomer that eluted first was identified as Compound 54 and was isolated as a light yellow oil (0.0054 g, 9%). The slower eluting isomer, Compound 55, was isolated as a light yellow solid (0.0107 g, 17% yield). Both: MS (M+1)=459 m/z.

EXAMPLE 56

Compound 56

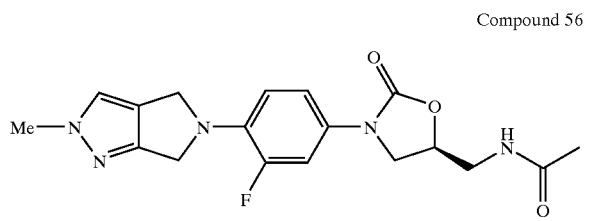

To Compound 44 (0.1098 g, 0.306 mmol) in DMF (4 mL) at RT was added sodium hydride (60% in oil) (0.018 g, 0.45 mmol) and the mixture stirred for 30 min whereupon MeI (23.0 µL, 0.369 mmol) was added. The mixture of regioisomers (as shown by $^1$H NMR) was stirred for 2 h and then poured into ice water. A ppt formed and was collected on a filter, dried in a vacuum oven (50° C.), and chromatographed on silica with 2.5% MeOH/CH$_2$Cl$_2$ as eluent to afford the product as a white solid (0.0215 g, 19%). Mp=234–238° C. MS (M+1)=374 m/z.

EXAMPLE 57

Compound 57

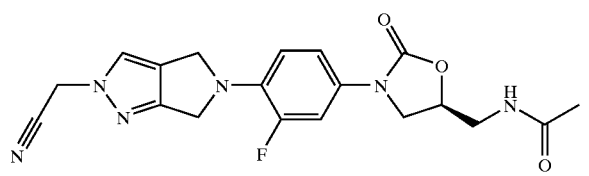

To Compound 44 (0.0701 g, 0.195 mmol) in DMF (3 mL) at RT was added sodium hydride (60% in oil) (0.014 g, 0.34 mmol) and the mixture stirred for 30 min whereupon chloroacetonitrile (17.5 µL, 0.276 mmol) was added. The mixture was stirred for 2 h and then poured into ice water. A ppt formed and was collected on a filter, dried in a vacuum oven (50° C.), and recrystallized from methanol to provide the product as a tan solid (0.0102 g, 13%). MS (M+1)=399 m/z.

EXAMPLE 58

Compound 58

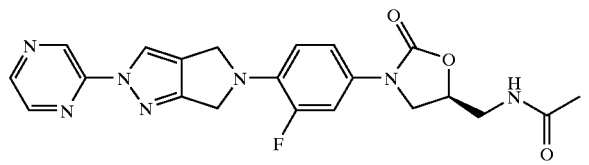

To Compound 44 (0.0744 g, 0.207 mmol) in DMF (3 mL) at RT was added sodium hydride (60% in oil) (0.015 g, 0.37 mmol) and the mixture stirred for 30 min whereupon chloropyrazine (26.5 µL, 0.299 mmol) was added. The mixture was stirred overnight and then poured into ice water. A ppt formed and was collected on a filter, dried in a vacuum oven (50° C.), and triturated with methanol to provide the product as a tan solid (0.0418 g, 46%). MS (M+1)=438 m/z.

EXAMPLE 59

Compound 59

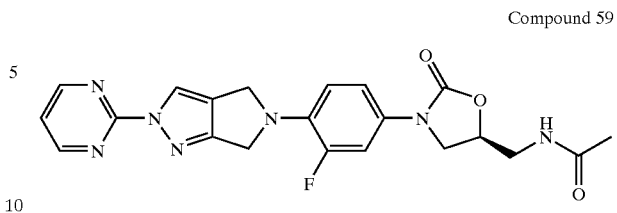

To Compound 44 (0.0676 g, 0.188 mmol) in DMF (3 mL) at RT was added sodium hydride (60% in oil) (0.018 g, 0.45 mmol) and the mixture stirred for 30 min whereupon 2-chloropyrimidine (0.0391 g, 0.324 mmol) was added. The mixture was stirred overnight and then poured into ice water. A ppt formed and was collected on a filter, dried in a vacuum oven (50° C.), and triturated with methanol to provide the product as a tan solid (0.0214 g, 26%). MS (M+1)=438 m/z.

EXAMPLE 60

Compound 60

Compound 61

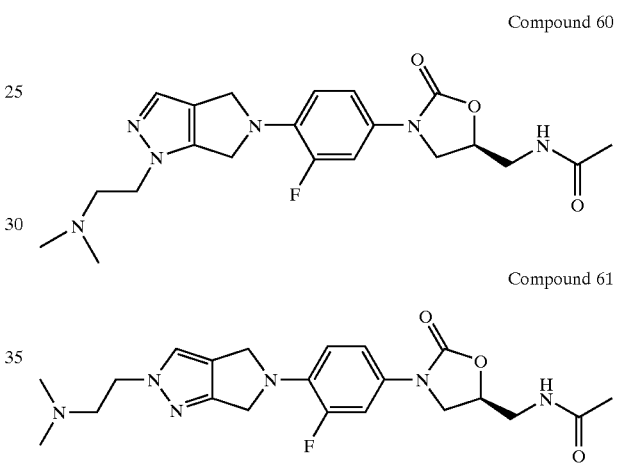

To Compound 44 (0.0712 g, 0.198 mmol) in DMF (3 mL) at RT was added KOtBu (in THF) (0.26 mL, 1.0 M) and the mixture stirred for 30 min whereupon 2-(methylamino)ethyl chloride (in benzene) (0.24 mL, 1.0 M) was added. The mixture was stirred overnight and then poured into ice water. The mixture was extracted with EtOAc (10×20 mL), dried over Na$_2$SO$_4$, concentrated and chromatographed on silica with 10% MeOH/CH$_2$Cl$_2$ as eluent to afford two products. The isomer that eluted first was identified as Compound 60 and was isolated as a light yellow glass (0.0074 g, 9%). The slower eluting isomer (Compound 61) was isolated as a light yellow glass (0.0269 g, 32% yield). Both: MS (M+1)=431 m/z.

EXAMPLE 61

Compound 62

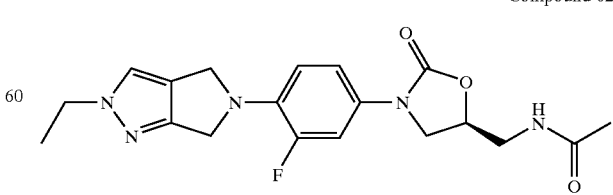

To Compound 44 (0.989 g, 0.275 mmol) in DMF (4 mL) at RT was added KOtBu (in THF) (0.36 mL, 1.0 M) and the mixture stirred for 30 min whereupon EtI (26.4 μL, 0.330 mmol) was added. The mixture was stirred for 2 h and then poured into ice water. A ppt formed, and was collected on a filter and dried in a vacuum oven (50° C.). The mixture of regioisomers (as shown by ¹H NMR) was chromatographed on silica with 2.5% MeOH/CH₂Cl₂ as eluent to afford the product as a white solid (0.0016 g, 2%). MS (M+1)=388 m/z.

EXAMPLE 62

Compound 63

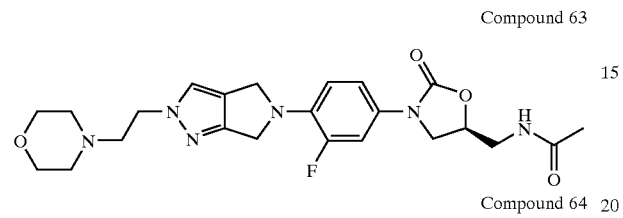

Compound 64

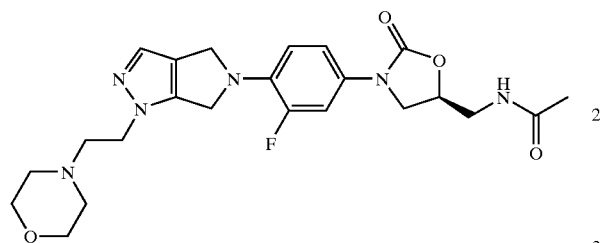

To Compound 44 (0.1120 g, 0.312 mmol) in DMF (3 mL) at RT was added KOtBu (in THF) (0.40 mL, 1.0 M) and the mixture stirred for 30 min whereupon 4-(2-chloroethyl) morpholine (in benzene) (0.37 mL, 1.0 M) was added. The mixture was stirred overnight and then poured into ice water. The mixture was extracted with EtOAc (10×20 mL), dried over Na₂SO₄, concentrated and chromatographed on silica with 5→10% MeOH/CH₂Cl₂ as eluent to afford the two products. The isomer that eluted first was identified as Compound 63 and was isolated as a light yellow glass (0.0102 g, 7%). The slower eluting isomer (Compound 64) was isolated as a light yellow solid (0.0518 g, 35% yield), Mp=180–190° C., decomp. Both: MS (M+1)=473 m/z.

EXAMPLE 63

Compound 65

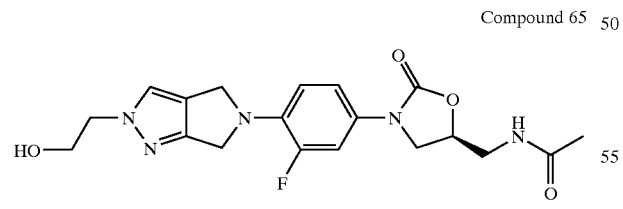

To Compound 44 (0.0793 g, 0.221 mmol) in DMF (2.5 mL) at RT was added Cs₂CO₃ (0.71 g, 2.2 mmols) and the mixture stirred for 15 min whereupon 2-chloroethanol (20 μL, 0.30 mmol) was added. The mixture was stirred overnight and then poured into ice water. A ppt formed and was collected on a filter and dried in a vacuum oven (50° C.) to provide the product as a light yellow solid (0.0632 g, 70%). Mp=232–242° C., decomp. MS (M+1)=404 m/z.

EXAMPLE 64

Compound 66

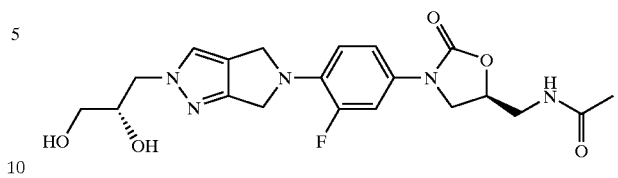

To Compound 44 (0.1546 g, 0.430 mmol) in DMF (3 mL) at RT was added Cs₂CO₃ (1.62 g, 5.0 mmols) and the mixture stirred for 15 min whereupon (R)-(−)-3-chloro-1,2-propanediol (45 μL, 0.54 mmol) was added. The mixture was stirred overnight and then poured into ice water. A ppt formed and was collected on a filter and dried in a vacuum oven (50° C.) to provide the product as a light yellow solid (0.1316 g, 70%). Mp=188–191° C. MS (M+1)=434 m/z.

EXAMPLE 65

Compound 67

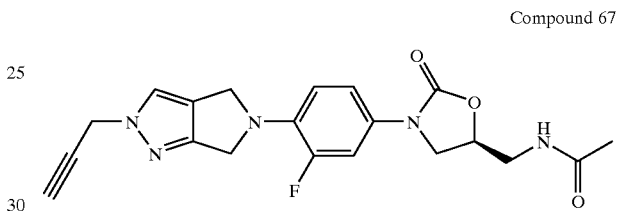

To Compound 44 (0.1524 g, 0.424 mmol) in DMF (3 mL) at RT was added KOtBu (in THF) (0.55 mL, 1.0 M) and the mixture stirred for 30 min whereupon propargyl bromide (80% in toluene) (0.06 mL, 0.54 mmol) was added. The mixture was stirred overnight at RT and then poured into ice water. A ppt formed and was collected on a filter and dried in a vacuum oven (50° C.) to provide 0.1483 g of a mixture of regioisomers (as shown by ¹H NMR). A portion of the crude material was chromatographed (40 mg in 0.5 mL DMSO) on reverse-phase HPLC with 5–30% acetonitrile/water containing 0.1%TFA as eluent. Pooled fractions containing Compound 67 were treated with 10% K₂CO₃ and the acetonitrile removed on a rotovap. A ppt formed and was collected on a filter and dried in a vacuum oven (50° C.) to provide the product as a white solid (0.0096 g, est. 21% yield). MS (M+1)=398 m/z.

EXAMPLE 66

Compound 68

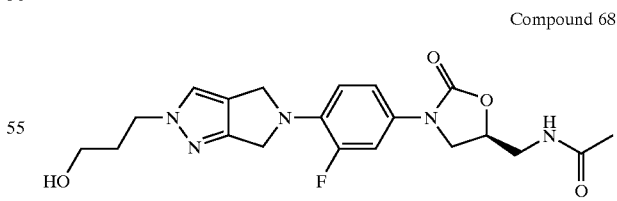

To Compound 44 (0.1460 g, 0.406 mmol) in DMF (3 mL) at RT was added Cs₂CO₃ (1.26 g, 3.87 mmols) and the mixture stirred for 15 min whereupon 3-chloropropanol (45 μL, 0.54 mmol) was added. The mixture was stirred overnight and then poured into ice water. A ppt formed and was collected on a filter and dried in a vacuum oven (50° C.) to provide the product as a light yellow solid (0.1526 g, 90%). Mp=171–173° C. MS (M+1)=418 m/z.

EXAMPLE 67

Compound 69

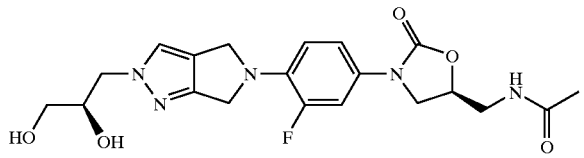

To Compound 44 (0.3523 g, 0.352 mmol) in DMF (3 mL) at RT was added Cs$_2$CO$_3$ (1.26 g, 3.87 mmols) and the mixture stirred for 15 min whereupon (S)-(+)-3-chloro-1,2-propanediol (37 µL, 0.44 mmol) was added. The mixture was stirred overnight and then poured into ice water. A ppt formed and was collected on a filter and dried in a vacuum oven (50° C.) to provide the product as a light brown solid (0.0862 g, 90%). Mp=184–188° C. MS (M+1)=434 m/z.

EXAMPLE 68

Compound 70

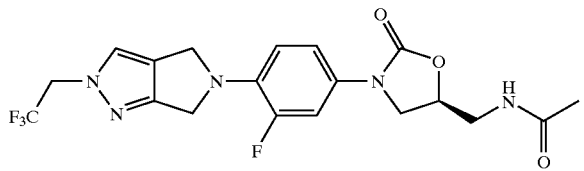

To Compound 44 (0.1070 g, 0.298 mmol) in DMF (2 mL) at RT was added CS$_2$CO$_3$ (0.97 g, 3.0 mmols) and the mixture stirred for 15 min whereupon 2-iodo-1,1,1-trifluoroethane (37 µL, 0.38 mmol) was added. The mixture was stirred three days whereupon an additional amount of 2-iodo-1,1,1-trifluoroethane (37 µL, 0.38 mmol) was added. After two days the mixture was poured into ice water. A ppt formed and was collected on a filter, dried in a vacuum oven (50° C.), and chromatographed on silica with 2.5→5% MeOH/CH$_2$Cl$_2$ as eluent to afford the product as a light yellow solid (0.0161 g, 12%). Mp=170–172° C. MS (M+1)=442 m/z.

EXAMPLE 69

Compound 71

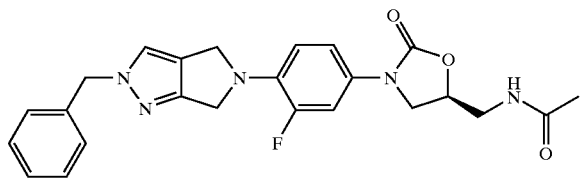

To Compound 44 (0.0530 g, 0.148 mmol) in DMF (1 mL) at RT was added KOtBu (in THF) (0.20 mL, 1.0 M) and the mixture stirred for 30 min whereupon benzylbromide (21 µL, 0.18 mmol) was added. The mixture was stirred overnight and then poured into ice water. A ppt formed and was collected on a filter and dried in a vacuum oven (50° C.) to provide 0.0521 g of a mixture of regioisomers (as shown by $^1$H NMR). The crude material was chromatographed on reverse-phase HPLC with 5–30% acetonitrile/water containing 0.1%TFA as eluent. Pooled fractions containing Compound 71 were treated with 10% K$_2$CO$_3$ and the acetonitrile removed on a rotovap. A ppt formed and was collected on a filter and dried in a vacuum oven (50° C.) to provide the product as a yellow solid (0.0111 g, 17% yield). MS (M+1)=450 m/z.

EXAMPLE 70

Compound 72

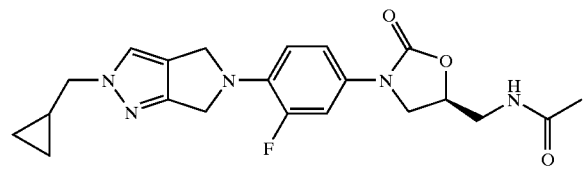

Compound 73

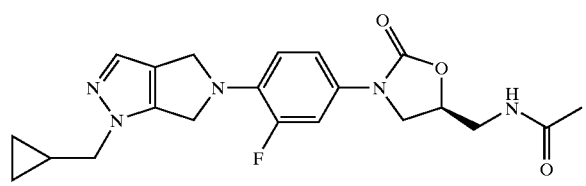

To Compound 44 (0.1065 g, 0.296 mmol) in DMF (2 mL) at RT was added KOtBu (in THF) (0.40 mL, 1.0 M) and the mixture stirred for 30 min whereupon (chloromethyl)cyclopropane (33 µL, 0.35 mmol) was added. The mixture was stirred overnight and then poured into ice water. A ppt formed and was collected on a filter and dried in a vacuum oven (50° C.) to provide 0.0868 g of a mixture of regioisomers. The crude material was chromatographed on silica with 5% MeOH/CH$_2$Cl$_2$ as eluent and then chromatographed (in 0.5 mL DMSO) on reverse-phase HPLC with 15–25% acetonitrile/water containing 0.1%TFA as eluent. Pooled fractions were treated with 10% K$_2$CO$_3$ and the acetonitrile removed on a rotovap. A ppt formed and was collected on a filter and dried in a vacuum oven (50° C.). The earlier eluting compound was identified as Compound 72 (0.0026 g, 2% yield). The later eluting compound was identified as Compound 73 (0.0082 g, 7%), a white solid Mp=234–236° C. Both: MS (M+1)=414 m/z.

EXAMPLE 71

Compound 74

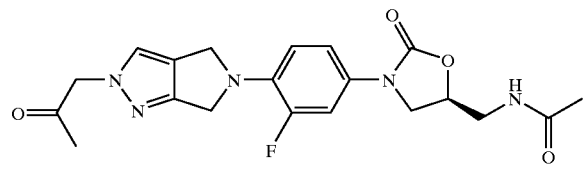

To Compound 44 (0.0.45 g, 0.125 mmol) in DMF (2 mL) at RT was added KOtBu (in THF) (0.16 mL, 1.0 M) and the mixture stirred for 30 min whereupon chloroacetone (13 µL, 0.16 mmol) was added. The mixture was stirred for seven days and resubjected to base and alkylating agent as before [KOtBu (in THF) (0.16 mL, 1.0 M) and chloroacetone (13 µL, 0.16 mmol)]. After two more days the mixture was poured into ice water. A ppt formed and was collected on a filter, dried in a vacuum oven (50° C.), and chromatographed on silica with 5% MeOH/CH$_2$Cl$_2$ as eluent to afford the product as a white solid (0.0087 g, 17%). MS (M+1)=416 m/z.

EXAMPLE 72

Compound 75

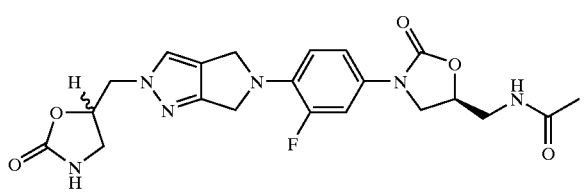

To Compound 44 (0.1018 g, 0.283 mmol) in DMF (2 mL) at RT was added $Cs_2CO_3$ (0.92 g, 2.8 mmols) and the mixture stirred for 30 min whereupon 5-chloromethyl-2-oxazolidinone (0.0511 g, 0.378 mmol) was added. The mixture was stirred at 60° C. for six days and then poured into ice water. A ppt formed and was collected on a filter and dried in a vacuum oven (5° C.) to provide 0.0429 g of a crude mixture. The crude material was chromatographed on reverse-phase HPLC with 5–30% acetonitrile/water containing 0.1%TFA as eluent. Pooled fractions were treated with 10% $K_2CO_3$ and the acetonitrile removed on a rotovap. A ppt formed and was collected on a filter and dried in a vacuum oven (50° C.)) to provide a white solid as a mixture of diastereomers (as indicated) (0.0054 g, 4%). MS (M+1)=459 m/z.

EXAMPLE 73

Compound 76

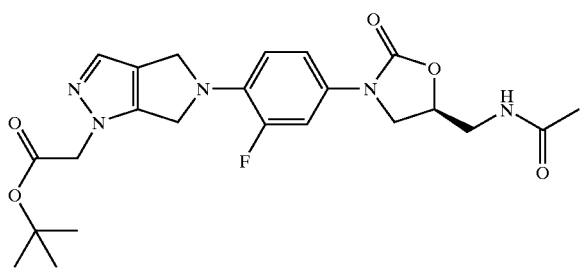

Compound 77

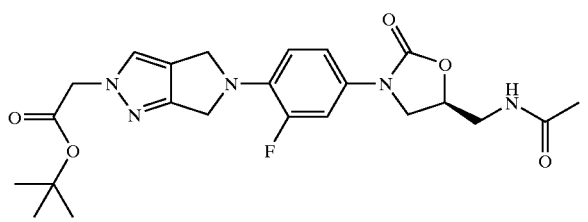

To Compound 44 (0.4566 g, 1.27 mmol) in DMF (10 mL) at RT was added KOtBu (in THF) (2.54 mL, 1.0 M) and the mixture stirred for 30 min whereupon tert-butyl bromoacetate (0.38 mL, 2.6 mmol) was added. The mixture was stirred overnight at 35° C. and then poured into ice water. A ppt formed and was collected on a filter and dried in a vacuum oven (50° C.) to provide 0.4404 g of a mixture of regioisomers. The crude material (200 mg) was chromatographed on reverse-phase HPLC with 5–20% acetonitrile/water containing 0.1%TFA as eluent. Pooled fractions were treated with 10% $K_2CO_3$ and the acetonitrile removed on a rotovap. A ppt formed and was collected on a filter and dried in a vacuum oven (50° C.). The earlier eluting compound was identified as Compound 76 (0.0032 g, 1%), a white solid Mp=85–90° C. The later eluting compound was identified as Compound 77 (0.0505 g, 18% yield) a white solid Mp=136–138° C. Both: MS (M+1)=474 m/z.

EXAMPLE 74

Compound 78

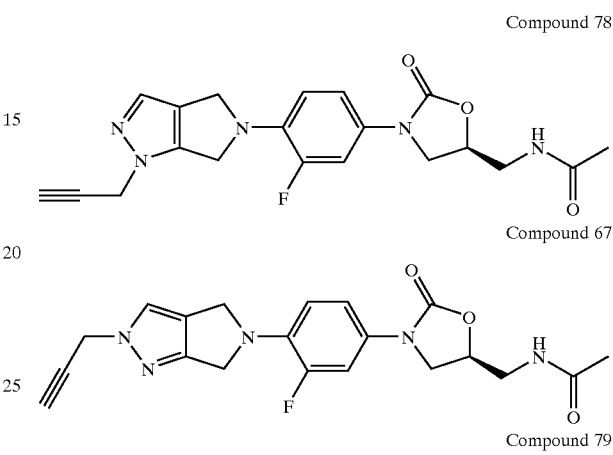

Compound 67

Compound 79

Compound 80

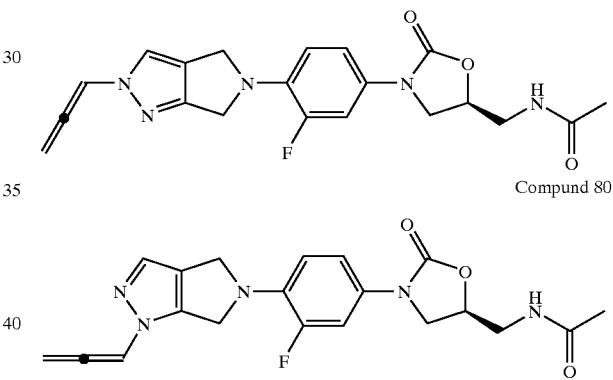

To Compound 44 (0.2689 g, 0.748 mmol) in DMF (6 mL) at 35° C. was added KOtBu (in THF) (1.50 mL. 1.0 M) and the mixture stirred for 15 min whereupon propargyl bromide (80% in toluene) (0.17 mL, 1.5 mmol) was added. The mixture was stirred overnight at 35° C. and then poured into ice water. A ppt formed and was collected on a filter and dried in a vacuum oven (50° C.). The crude material was chromatographed on reverse-phase HPLC with 5–25% acetonitrile/water containing 0.1%TFA as eluent. Pooled fractions were treated with 10% $K_2CO_3$ and the acetonitrile removed on a rotovap. A ppt formed and was collected on a filter and dried in a vacuum oven (50° C.). Four compounds were separable in the following order, earlier to later eluting: the first compound was identified as Compound 78 (0.0082 g, 3%), a white solid Mp=140–142° C.; the second compound was identified as the previous synthesized Compound 67 (0.0734 g, 25%), a white solid; the third compound was identified as Compound 79 (0.0101 g, 3%), a white solid Mp=180–182° C.; the fourth compound was identified as Compound 80 (0.0062 g, 3%), a white solid Mp=183–186° C. All: MS (M+1)=398 m/z.

EXAMPLE 75

Compound 81

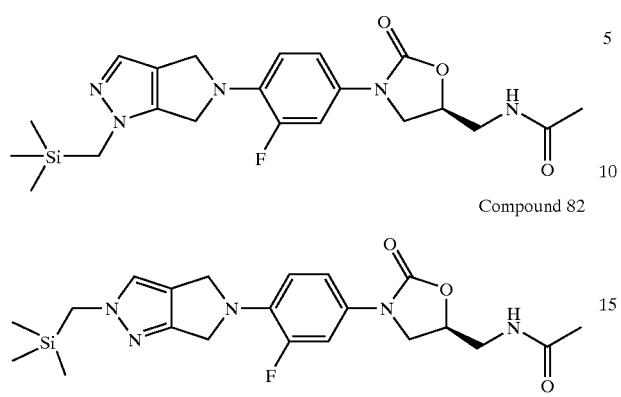

Compound 82

To Compound 44 (0.0766 g, 0.213 mmol) in DMF (1.5 mL) at RT was added KOtBu (in THF) (0.43 mL, 1.0 M) and the mixture stirred for 30 min whereupon chloromethyltrimethylsilane (61 µL, 0.44 mmol) was added. The mixture was stirred overnight at RT and then poured into ice water. A ppt formed and was collected on a filter, dried in a vacuum oven (50° C.), and chromatographed on reverse-phase HPLC with 5–50% acetonitrile/water containing 0.1%TFA as eluent. Pooled fractions were treated with 10% $K_2CO_3$ and the acetonitrile removed on a rotovap. A ppt formed and was collected on a filter and dried in a vacuum oven (50° C.). The earlier eluting compound was identified as Compound 81 (0.0148 g, 16%), a white solid Mp=148–150° C. The later eluting compound was identified as Compound 82 (0.0217 g, 23% yield) a white solid Mp=151–153° C. Both: MS (M+1)=446 m/z.

EXAMPLE 76

Compound 83

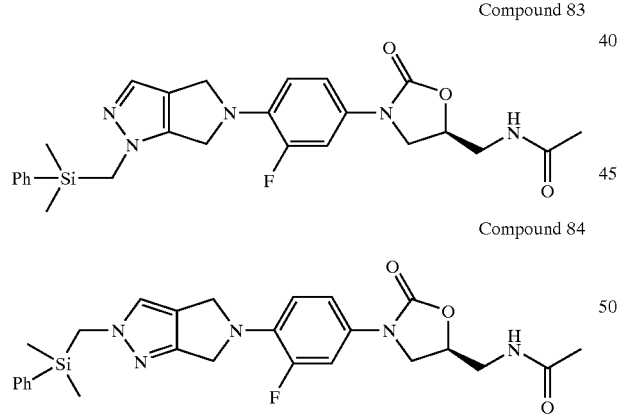

Compound 84

To Compound 44 (0.1050 g, 0.292 mmol) in DMF (2 mL) at RT was added KOtBu (in THF) (0.58 mL, 1.0 M) and the mixture stirred for 30 min whereupon (chloromethyl)dimethylphenylsilane (0.12 mL, 0.66 mmol) was added. The mixture was stirred overnight at RT and then poured into ice water. The mixture was extracted with EtOAc (6×16 mL), dried over $Na_2SO_4$, and concentrated. The crude material was chromatographed on reverse-phase HPLC with 5–50% acetonitrile/water containing 0.1%TFA as eluent. Pooled fractions were treated with 10% $K_2CO_3$ and the acetonitrile removed on a rotovap. A ppt formed and was collected on a filter and dried in a vacuum oven (50° C.). The earlier eluting compound was identified as Compound 83 (0.0026 g, 2%), a white solid. The later eluting compound was identified as Compound 84 (0.0064 g, 4% yield) a white solid. Both: MS (M+1)=508 m/z.

EXAMPLE 77

Compound 85

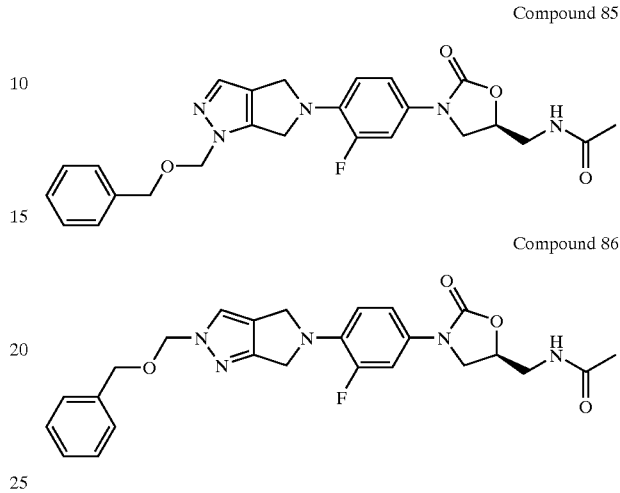

Compound 86

To Compound 44 (0.0998 g, 0.278 mmol) in DMF (1.5 mL) at RT was added KOtBu (in THF) (0.42 mL, 1.0 M) and the mixture stirred for 30 min whereupon benzyl chloromethyl ether (62.1 µL, 0.417 mmol) was added. The mixture was stirred overnight at 35° C. and then poured into ice water. A ppt formed and was collected on a filter and dried in a vacuum oven (50° C.) to provide 0.1157 g of a mixture of regioisomers. The crude material was chromatographed on reverse-phase HPLC with 5–30% acetonitrile/water containing 0.1%TFA as eluent. Pooled fractions were treated with 10% $K_2CO_3$ and the acetonitrile removed on a rotovap. A ppt formed and was collected on a filter and dried in a vacuum oven (50° C.). The earlier eluting compound was identified as Compound 85 (0.0120 g, 9%), a white solid Mp=127–130° C. The later eluting compound was identified as Compound 86 (0.0262 g, 20% yield) a white solid Mp=156–159° C. Both: MS (M+1)=480 m/z.

EXAMPLE 78

Compound 87

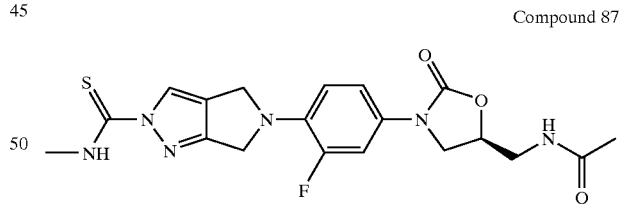

To Compound 44 (0.2983 g, 0.830 mmol) in DMF (9 mL) at RT was added KOtBu (in THF) (1.0 mL, 1.0 M) and the mixture stirred for 30 min whereupon methyl isothiocyanate (0.11 mL, 1.6 mmol) was added. The mixture was stirred overnight at RT and then poured into ice water. A ppt formed and was collected on a filter and dried in a vacuum oven (50° C.) to provide 0.2903 g of crude material. A portion of the material (100 mg) was chromatographed on reverse-phase HPLC with 5–25% acetonitrile/water containing 0.1%TFA as eluent. Pooled fractions were treated with 10% $K_2CO_3$ and the acetonitrile removed on a rotovap. A ppt formed and was collected on a filter and dried in a vacuum oven (50° C.). Compound 87 was isolated as a tan solid (0.0162 g, 13% yield). Mp=246–249° C. MS (M+1)=433 m/z.

EXAMPLE 79

Compound 88

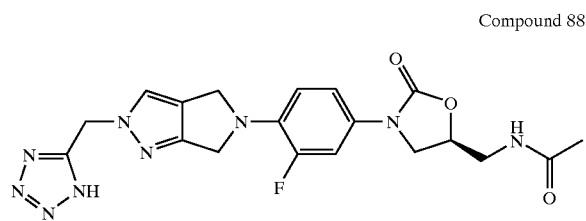

To Compound 57 from Example 57 (0.0955g, 0.240 mmol) in DMF (1 mL) at RT was added dibutyltin oxide (0.0065 g, 0.03 mmol) and then azidotrimethylsilane (64 μL, 0.48 mmol). The mixture was stirred overnight at 100° C. and then poured into ice water. A ppt formed and was collected on a filter, dried in a vacuum oven (50° C.), and chromatographed on silica with 10 MeOH/CH$_2$Cl$_2$ containing 1% acetic acid as eluent. The product was isolated as a tan solid (0.0379 g, 36% yield). MS (M+1)=442 m/z.

EXAMPLE 80

Compound 89

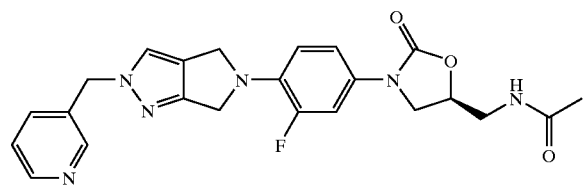

To Compound 44 (0.110 g, 0.306 mmol), and Cs$_2$CO$_3$ (1.03 g, 3.03 mmol) in DMF (15 mL) was added 3-picolyl chloride hydrochloride. After stirring at RT for 20 hr the reaction was poured into water and extracted with EtOAc (3×30 mL). The organic phases were washed with water and brine, dried over Na$_2$SO$_4$, and concentrated in vacuo to an orange film. The mixture was purified by column chromatography on silica using 5% methanol/ethyl acetate to afford a mixture of regioisomers (as shown by $^1$H NMR). Compound 89 could be purified by preparative reverse-phase HPLC and was isolated as a white powder (7%). MS=451 (M+H).

EXAMPLE 81

Compound 90

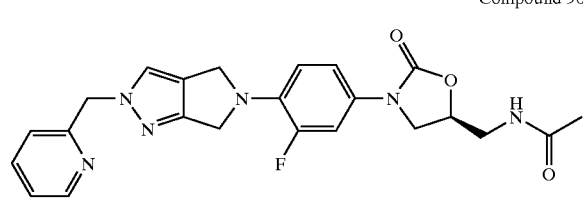

Compound 91

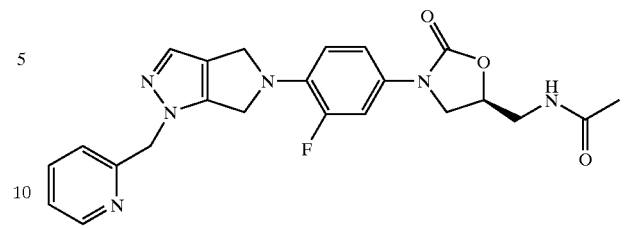

The two regioisomers were synthesized by the above procedure, using 2-picolyl chloride hydrochloride. After preparative reverse-phase HPLC purification, Compound 90 was isolated as a yellow solid (6%) and Compound 91 was isolated as a yellow film (2%). Both MS=451 (M+H)

EXAMPLE 82

Compound 92

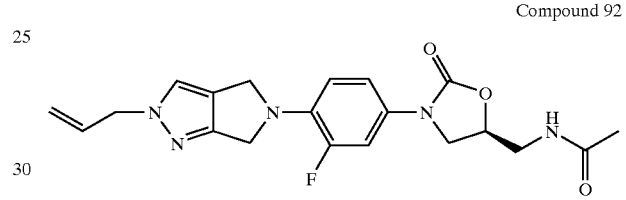

To Compound 44 (0.051 g, 0.143 mmol), in DMF (5 mL) was added KOt-Bu (0.17 mL, 1 M in THF). The reaction was stirred at RT for 10 min, and then allyl bromide (0.014 mL. 0.16 mmol) was added. After 20 minutes the reaction was poured into water, and extracted with EtOAc (3×50 mL). The combined organics were washed with water, brine, and then dried over MgSO$_4$. The mixture of regioisomers (as shown by $^1$H NMR) was concentrated in vacuo to a yellow residue, and purified by preparative reverse-phase HPLC to give a colorless film to provide Compound 92 (3%). MS=438 (K+).

EXAMPLE 83

Compound 93

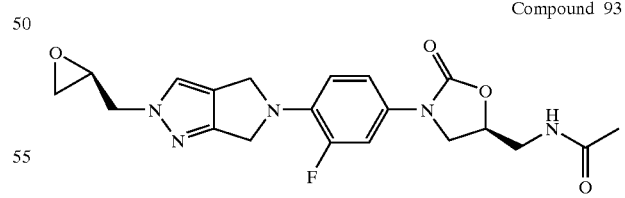

To Compound 44 (1.15 g, 3.20 mmol), in DMF (10 mL) was added (S)-epichlorohydrin (0.28 mL, 3.5 mmol), followed by the dropwise addition of KOt-Bu (3.84 mL, 1.0 M in THF) at RT. After 3 hr, the reaction was poured into water (40 mL) and a fine, white powder precipitated from solution. The powder was collected by filtration, washed with water, and dried in vacuo at 50° C. to give the product as a single stereoisomer in 63% yield. MS=454 (K+).

EXAMPLE 84

Compound 94

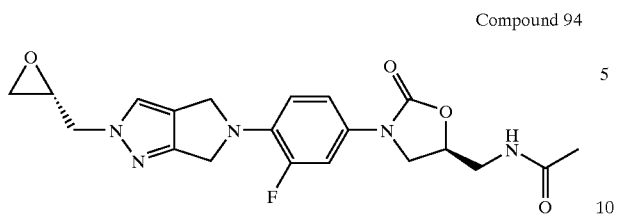

To Compound 44 (0.050 g, 0.139 mmol), in DMF (5 mL) was added (R)-epichlorohydrin (0.01 mL, 0.2 mmol), followed by the dropwise addition of KOt-Bu (0.17 mL, 1.0 M in THF) at RT. After 3 hr, the reaction was poured into water (40 mL) and extracted with EtOAc (3×30 mL). The combined organics were washed with water, then brine and dried over $MgSO_4$. The filtrate was concentrated in vacuo to provide the crude product as a yellow solid. The solid was chromatographed on silica using 3% methanol/methylene chloride to elute the product as a single stereoisomer. Compound 94 was isolated as a yellow powder (37%). MS=416 (M+H), 438 (Na+).

EXAMPLE 85

Compound 95

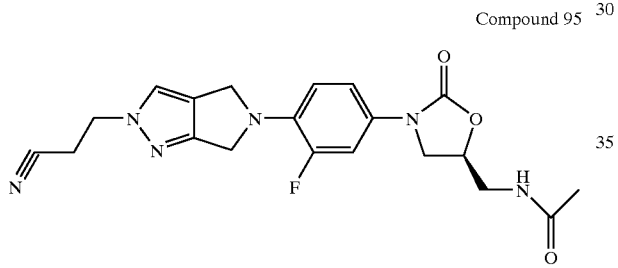

To Compound 44 (0.048 g, 0.13 mmol), in DMF (1 mL) was added $K_2CO3$ (0.074 g, 0.54 mmol) and bromopropionitrile (0.013 mL, 0.16 mmol) and the reaction was heated to 50° C. for 40 minutes. Upon cooling, the reaction was added to water (6 mL) and extracted with EtOAc (3×10 mL). The extracts were washed with water, then brine and dried over $MgSO_4$. The filtrate was concentrated in vacuo. The crude product was chromatographed on silica with 4% methanol/ethyl acetate as eluent to provide Compound 95 (18%). MS=413 (M+H), 435 (Na+).

EXAMPLE 86

Compound 96

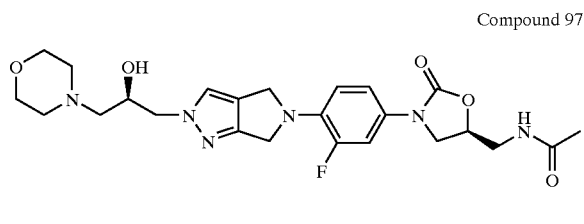

Compound 93 (0.050 g, 0.120 mmol) was dissolved in excess piperdine (1 mL) and refluxed for 20 hr. The reaction mixture was concentrated in vacuo and the resulting residue was extracted with EtOAc (3×10 mL). The organics were washed with water and brine, and dried over $Na_2SO_4$. The filtrate was concentrated in vacuo to an orange oil that was purified by silica gel column chromatography. The product eluted with 10% methanol/methylene chloride to give a white solid in 20% yield. MS=501. (M+H), 523 (Na+).

EXAMPLE 87

Compound 97

Compound 93 (0.052 g, 0.124 mmol) was dissolved in excess morpholine (1 mL) and refluxed for 20 hr. The reaction mixture was concentrated in vacuo and the resulting residue was extracted with EtOAc (3×10 mL). The organics were washed with water and brine, and dried over $Na_2SO_4$. The filtrate was concentrated in vacuo to an orange oil that was purified by silica gel column chromatography. The product eluted with 5% methanol/methylene chloride to give Compound 97 as a white solid in 20% yield. MS=503.3 (M+H), 525.3 (Na+).

EXAMPLE 88

Compound 98

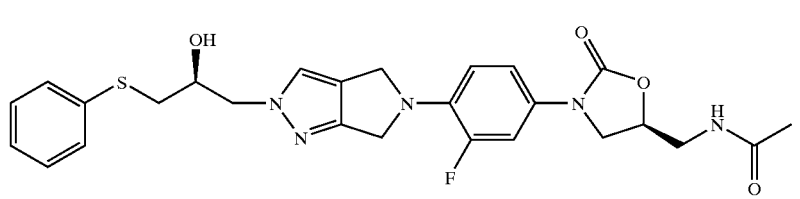

The sodium salt of benzenethiol (0.0456 g, 0.345 mmol) was added to a solution of Compound 93 (0.120 g, 0.288 mmol) in DMF (10 mL) RT. Upon completion of the reaction as judged by thin layer chromatography, the reaction mixture was poured into water and extracted with EtOAc (3×10 mL). The extracts were washed with water, then brine, and dried over MgSO$_4$. The filtrate was concentrated in vacuo to afford an off-white solid in 7% yield. MS=526 (M+H), 548 (Na+).

EXAMPLE 89

Compound 99

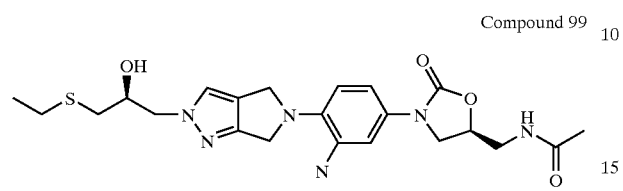

To a solution of Compound 93 (0.102 g, 0.246 mmol) in DMF (4 mL) was added Cs$_2$CO$_3$ (0.802 g, 2.46 mmol), followed by the dropwise addition of ethanethiol (0.02 mL, 0.295 mmol). After stirring for 3 hr at RT water (15 mL) was added and the reaction mixture was extracted with EtOAc (3×10 mL). The combined organic extracts were washed with water, then brine, and dried over MgSO$_4$. The filtrate was concentrated in vacuo to give the crude product as a yellow film. Trituration with methylene chloride/hexanes gave the product as a gold solid (3%). MS=478 (M+H), 500 (Na+).

EXAMPLE 90

Compound 100

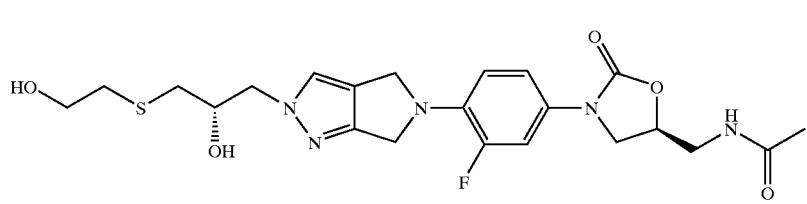

To a solution of Compound 94 (0.0921 g, 0.222 mmol) in DMF (4 mL) was added Cs$_2$CO$_3$ (0.722 g, 2.22 mmol) followed by the dropwise addition of mercaptoethanol (0.02 mL, 0.266 mmol). The reaction mixture was stirred RT for 20 hr. Water (15 mL) was poured into the reaction and the resulting mixture was, extracted with EtOAc (3×10 mL). The combined extracts were washed with water, then brine, and dried over MgSO$_4$. The filtrate was concentrated in vacuo and purified by silica gel column chromatography, using 10% methanol/methylene chloride to elute the product (3%). MS=516 (Na+).

EXAMPLE 91

Compound 101

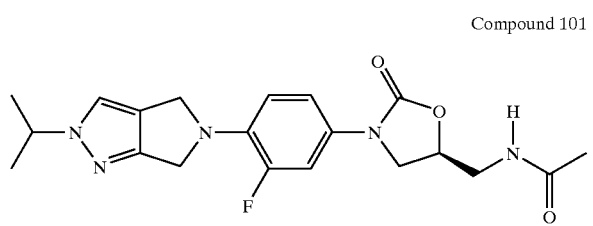

To a DMSO(3 mL) solution of Compound 44 (0.123 g, 0.343 mmol), was added 2-propyl bromide (0.04 mL, 0.411 mmol), followed by dropwise addition of KOt-Bu (0.41 mL, 0.411 mmol, 1 M in THF). The reaction mixture was stirred at RT for 20 hr, poured into water (15 mL) and extracted with EtOAc (3×15 mL). The combined organics were washed with water, then brine and dried over Na$_2$SO$_4$. The filtrate was concentrated in vacuo to give a mixture of starting material and the desired product as a yellow oil. These two compounds were separated by preparative reverse-phase HPLC to give Compound 101 (2%). MS=440 (K+).

EXAMPLE 92

Compound 102

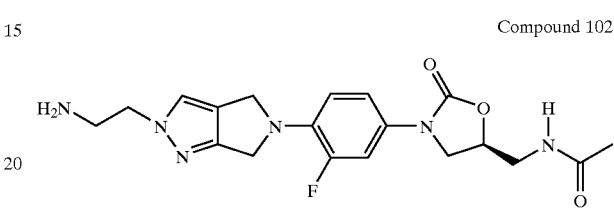

Mesylate Formation:

To a suspension of Compound 65 (0.0521 g, 0.129 mmol) in DMF (5 mL) was added triethylamine (0.04 mL, 0.3 mmol) followed by methanesulfonyl chloride (0.01 mL, 0.2 mmol). The reaction was stirred at RT for 2 hr. At this time, the reaction was poured into water (20 mL) and extracted with EtOAc (3×20 mL). The combined organics were washed with water, then brine and dried over MgSO$_4$. The filtrate was concentrated in vacuo to give a gold residue. The mesylate was used in the next reaction without further purification.

Phthalimide Formation:

To a DMF (10 mL) solution of the above compound (0.060 g, 0.12 mmol) was added potassium phthalimide (0.046 g, 0.25 mmol) and the reaction was heated to 60° C. After heating for 20 hr the solution was cooled to RT and poured into water (40 mL), extracted with EtOAc (3×20 mL), and the organics were washed with water and brine. After drying over MgSO$_4$, the organics were concentrated to an orange solid, then purified by silica gel column chromatography. The desired phthalimide was eluted from the column with 5% methanol/methylene chloride in 14% yield.

Amine Formation:

To a methanol solution containing the phthalimide compound from above (0.0095 g, 0.018 mmol) was added hydrazine monohydrate (0.010 mL, 0.036 mmol) and the reaction mixture was heated to reflux for 10 hr. The methanol was removed in vacuo and the reaction was dissolved in EtOAc (10 mL), washed with water, and then brine. The organics were then dried over MgSO$_4$, and the filtrate was concentrated to a gold film. The residue was triturated with 5% methanol/ethyl acetate to remove impurities and provide the product as a pale yellow film (20%). MS=403 (M+H), 425 (Na+).

EXAMPLE 93

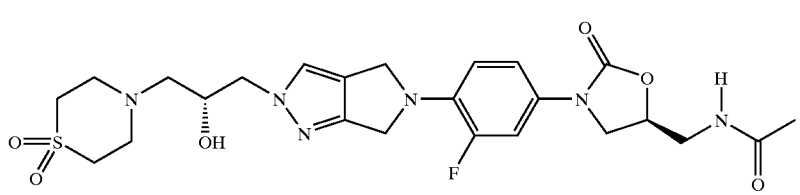

Compound 103

Formation of the Thiomorpholine Compound:

To a solution of Compound 93 (0.147 g, 0.353 mmol) in DMF (5 mL) at 60° C. was added thiomorpholine (0.18 mL, 1.76 mmol) and the reaction was heated to 85° C. for five hours. After cooling to RT, water (15 mL) was added and an off-white precipitate formed which was collected by vacuum filtration and discarded. The filtrate was extracted with EtOAc (3×40 mL) and the extracts were washed repeatedly with water to remove residual DMF. The organic portion was dried over $Na_2SO_4$ and the filtrate was concentrated in vacuo to a yellow film. The sulfide was isolated in 30% yield and used without further purification.

Formation of the Sulfone:

The compound from above (0.053 g, 0.03 mmol) was taken up in methylene chloride (5 mL) and m-CPBA (77% peroxide) (0.069 g, 0.31 mmol) was added to the solution at RT. After 3 hr the reaction was quenched with aqueous $NaHCO_3$, and a white precipitate formed. The solid was collected by vacuum filtration and dried to recover the sulfone (7%). MS=573 (Na+).

EXAMPLE 94

Compound 104

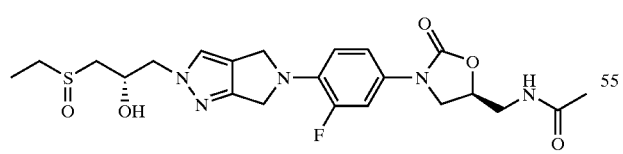

Formation of the Sulfide:

To Compound 93 (0.130 g, 0.313 mmol) in DMF (7 mL) was added $Cs_2CO_3$ (0.510 g, 1.56 mmol) followed by ethanethiol (0.03 mL, 0.4 mmol) at RT and the reaction was stirred for 3 hr. The reaction mixture was diluted with water and the aqueous portion was extracted with EtOAc (3×20 mL). The combined organics were dried over $MgSO_4$ and the filtrate was concentrated to give a white film. The crude product was purified using silica gel column chromatography, eluting the pure product (23%) with 5% methanol/ethyl acetate.

Formation of the Sulfoxide:

The sulfide from above (0.0162 g, 0.0340 mmol) was dissolved in methylene chloride (2 mL) and (Polystyrylmethyl) trimethylammonium metaperiodate (0.0283 g, 2.40 mmol/g) (Novabiochem®) was added. The reaction was stirred gently for 20 hr at RT. The resin was removed by filtration, and washed with methylene chloride. The filtrate was concentrated in vacuo to give a crude mixture of products. The sulfoxide was purified by silica gel column chromatography, eluting with 10% methanol/EtOAc. The resulting product was a diastereomeric mixture of sulfoxides. MS=494 (M+H), 516 (Na+).

EXAMPLE 95

Compound 105

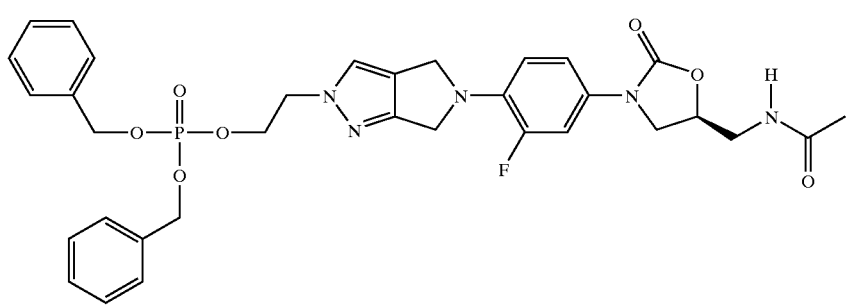

A suspension of Compound 65 (0.4468 g, 1.11 mmols) in THF (2 mL) was cooled to −78° C. and LDA (0.72 mL, 2.0 M in THF) was added dropwise. After 15 min, tetrabenzylpyrophosphate (0.7753 g, 1.44 mmol) was added and the mixture was stirred for 30 min at −78° C. The reaction mixture was allowed to warm to RT and was then stirred for 24 hr. The crude product was chromatographed on silica and the product (40%) eluted with 2% methanol/methylene chloride. MS=664 (M+H), 686 (Na+).

EXAMPLE 96

Compound 106

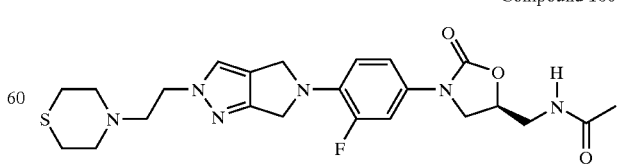

To the crude mesylate from Example 92 (0.087 g, 0.181 mmol) in DMF (10 mL) was added thiomorpholine (0.055 mL, 0.543 mmol) and the reaction was heated to 80° C. for 20 hr. Upon cooling the reaction mixture was poured into water and extracted with EtOAc (3×40 mL). The combined organics were washed with water, brine, and then dried over MgSO$_4$. The mixture was filtered and concentrated in vacuo to give a gold oil. The oil was purified using silica gel column chromatography eluting with 10% methanol/ethyl acetate gave Compound 106 in 9% yield. MS=489 (M+H), 511 (Na+).

20 hr. The reaction mixture was diluted with methylene chloride and washed with water. The organic solution was dried over Na$_2$SO$_4$, filtered and concentrated to a yellow solid. Silica gel column chromatography was used to purify the product with 3% methanol/methylene chloride as the eluent. The Compound 109 was isolated, after trituration with EtOAc, as a white solid in 12% yield. MS=452 (M+H), 474 (Na+).

EXAMPLE 97

Compound 107

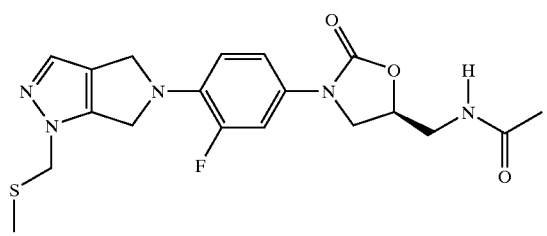

EXAMPLE 99

Compound 110

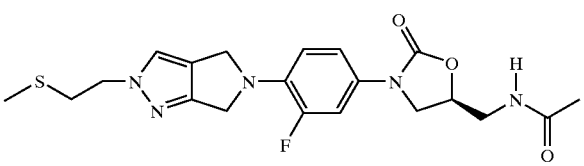

Compound 108

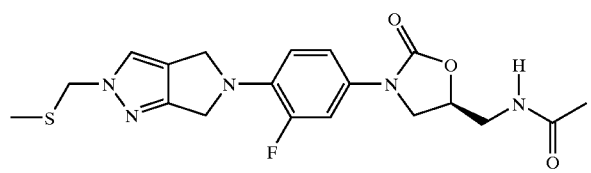

To a suspension of Compound 65 (0.1185 g, 0.294 mmol) in DMF (5 mL) was added triethylamine (0.090 mL, 0.65 mmol) followed by methanesulfonyl chloride (0.03 mL, 0.4 mmol). After stirring at RT for 30 min sodium thiomethoxide (0.0247 g, 0.352 mmol) was added directly to the reaction mixture which was heated to 50° C. for 3 hours. The mixture was poured into water (20 mL) and extracted with EtOAc (3×10 mL). The combined organics were washed with water, then brine and dried over Na$_2$SO$_4$. The filtrate was concentrated in vacuo to afford an orange oil in approximately 38% yield, which was used without further purification in the next reaction. MS=434 (M+H), 456 (Na+).

To a DMF (20 mL) solution of Compound 44 (0.4126 g, 1.148 mmols), at 37° C. was added KOt-Bu (2.3 mL, 1.0 M in THF) and the reaction mixture was stirred for 20 min. To this mixture was added chloromethyl methyl sulfide (0.15 mL, 1.7 mmols) and the reaction was stirred for 20 hr. The reaction mixture was poured into water and a precipitate formed. The solid was collected by vacuum filtration and dried for several hours under vacuum at 50° C. The two regioisomers were separated by preparative reverse-phase HPLC to give Compound 107 in a 6% yield and Compound 108 in a 12% yield. MS=420 (M+H), 442 (Na+).

EXAMPLE 100

Compound 111

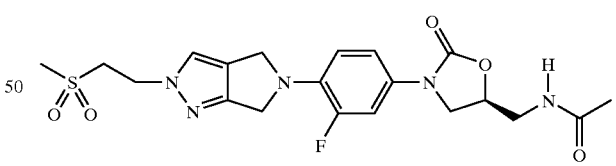

EXAMPLE 98

Compound 109

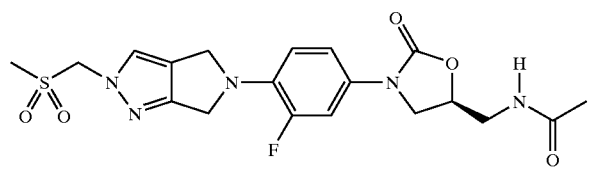

To Compound 108 (0.0540 g, 0.1289 mmol) in methylene chloride (5 mL) was added tetrabutylammonium oxone (0.3517 g, 0.3866 mmol). The solution was stirred at RT for The crude oil from Example 99 (0.0982 g, 0.226 mmol) was dissolved in methylene chloride (10 mL) and tetrabutylammonium oxone (0.2321 g, 0.680 mmol) was added. The reaction mixture was stirred at RT for 5 hr and then diluted with methylene chloride. The organic portion was washed with water several times, and dried over Na$_2$SO$_4$. The organic solution was concentrated to a yellow solid and purified by silica gel column chromatography. The product was eluted with 3% methanol/methylene chloride to provide the product in 2% yield. MS=466 (M+H), 488 (Na+).

EXAMPLE 101

Compound 112

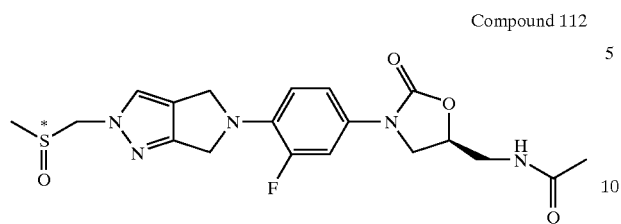

Compound 113

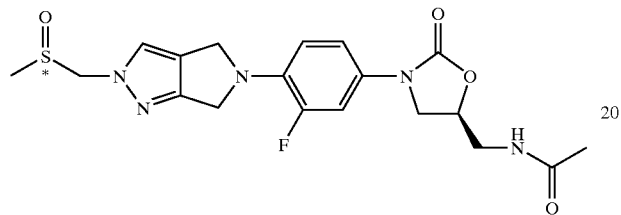

A methylene chloride (15 mL) solution of Compound 108 (0.0758 g, 0.181 mmol) was cooled to −78° C. before adding m-CPBA (0.0405 g, 0.181 mmol) as a methylene chloride solution, dropwise, over 20 min. The reaction mixture was stirred for another 30 min at −78° C., then warmed to room temperature. The mixture was washed with aqueous sodium bicarbonate, brine, and then dried over sodium sulfate. The filtrate was concentrated in vacuo to a yellow solid, and then purified by HPLC to give the separate diastereomeric sulfoxide products of undetermined stereochemistry, 12% overall yield. MS=436 (M+H), 458 (Na+).

EXAMPLE 102

Compound 114

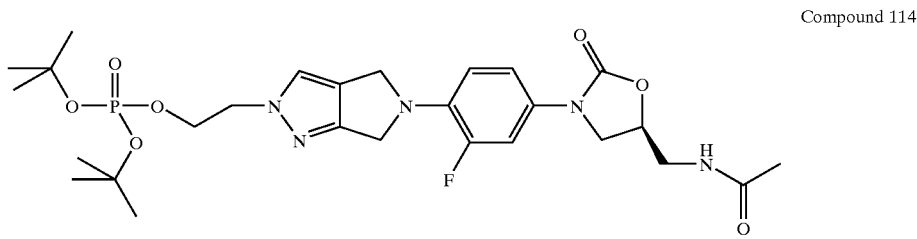

Di-t-butyl N,N-diethylphosphoramidite (0.13 mL, 0.45 mmol) was added dropwise to a stirred suspension of Compound 65 (0.1134 g, 0.281 mmol) in THF and 1H-tetrazole (0.1969 g, 2.81 mmol) at RT under nitrogen. The reaction was stirred at RT for 2.5 hr. After cooling the reaction mixture to −78° C., m-CPBA (0.0631 g, 0.281 mmol) was added in several portions. The mixture was stirred for 1 hr at −78° C., then warmed to RT for another hour.

The reaction mixture was diluted with EtOAc and washed successively with 10% aqueous sodium bisulfite, saturated aqueous NaHCO₃, and water. The combined organics were dried over MgSO₄, filtered, and concentrated to a tan oil. The crude oil was chromatographed on silica and Compound 114 was eluted with 5% methanol/EtOAc and concentrated to provide a pale yellow film (7%). MS=596 (M+H), 618 (Na+).

EXAMPLE 103

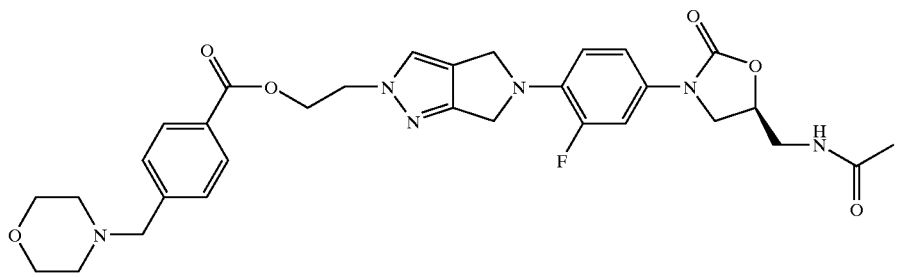

Compound 115

Benzyl Chloride Formation:

To Compound 65 (0.0594 g, 0.147 mmol) suspended in a 2:1 solution of methylene chloride/acetonitrile was added triethylamine (0.10 mL, 0.74 mmol), followed by (4-chloromethyl)benzoyl chloride (0.035 g, 0.18 mmol). The reaction mixture was stirred at RT for 3 hr. The solvent was removed and water was added to precipitate a yellow solid. The solid was collected by filtration and dried to a pale yellow powder. The product was used without further purification.

Final Product:

To a mixture of the benzyl chloride, described above, (0.040 g, 0.074 mmol) in DMF (5 mL) was added NaI (0.005 g) and morpholine (0.050 mL, 0.56 mmol) at 50° C. for 20 hr. The reaction mixture was poured into water, and extracted with methylene chloride (3×15 mL) and the combined organics were washed with water, then brine, and dried over MgSO$_4$. The organic layer was filtered and concentrated in vacuo to a yellow solid. Compound 115 was purified by silica gel column chromatography and eluted with 5% methanol/methylene chloride as a white film (27%). MS=607 (M+H)/

EXAMPLE 104

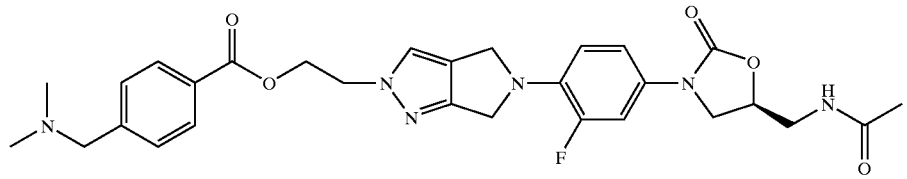

Compound 116

To a mixture of the benzyl chloride (prepared as in Example 103) (0.1280 g, 0.230 mmol) in DMF (10 mL) was added NaI (0.005 g) and dimethylamine (0.92 mL, 2.0 M in MeOH,), at 50° C. for 1 hr. Methanol was removed in vacuo, and the reaction mixture was diluted with methylene chloride before being washed with water and brine. The combined organics were dried over MgSO$_4$, and concentrated in vacuo to a yellow waxy solid. The crude product was purified by silica gel column chromatography eluting with 2% methanol/methylene chloride. Further purification was achieved by preparative reverse phase HPLC to provide Compound 116 as a white powder (3%). MS=565 (M+H).

EXAMPLE 105

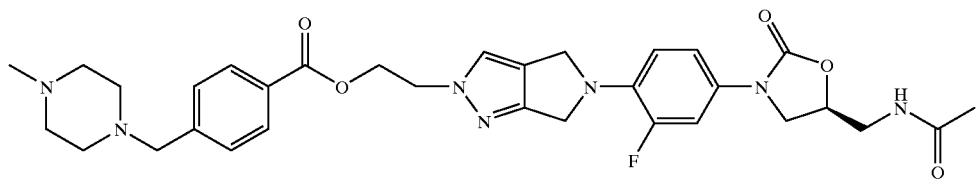

Compound 117

To a mixture of the benzyl chloride (as prepared in Example 103)(0.1330 g, 0.239 mmol) in DMF (10 mL) was added NaI (0.010 g) and N-methyl piperdine (0.13 mL, 1.2 mmol) at 50° C. for 2 hr. The reaction mixture was poured into water and extracted with EtOAc (3×15 mL). The combined organics were washed with water, brine, and dried over MgSO$_4$. The organic layer was filtered and concentrated in vacuo to a yellow film. Compound 117 was purified by silica gel column chromatography and eluted with 10% methanol/methylene chloride as a yellow film (2%). MS=620 (M+H).

EXAMPLE 106

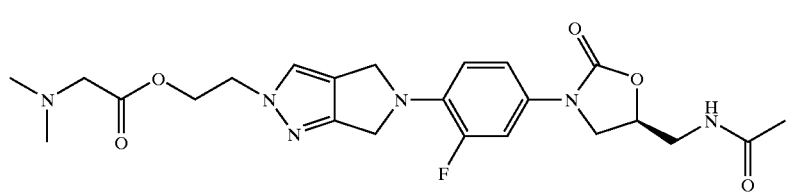

Compound 118

A slurry of DCC (0.5033 g, 0.496 mmol), N,N-dimethylglycine (0.1020 g, 0.992 mmol), and DMAP (0.0606 g, 0.496 mmol) in methylene chloride was stirred for 5 min at RT before adding Compound 65. The reaction mixture was stirred at RT for 24 h, diluted with methylene chloride and washed with water. The organics were dried over $MgSO_4$ and concentrated to a yellow oil. The oil was triturated with EtOAc to give a white solid which was collected by filtration. The filtrate was concentrated to a yellow oil, and purified by silica gel column chromatography, eluting with 2% methanol/methylene chloride (2%). MS=489 (M+H), 511 (Na+).

EXAMPLE 107

A mixture of EDCI (0.950 g, 4.96 mmol), DMAP (0.121 g, 0.992 mmol) and carbobenzyloxy-L-valine was stirred for 15 min at RT in 20 mL methylene chloride. Compound 65 (0.400 9, 0.992 mmol) was added and the reaction mixture was stirred at RT for several hours. The mixture was diluted with water and extracted with methylene chloride (3×30 mL). The combined extracts were washed with water, brine, and then dried over $Na_2SO_4$. The crude product was concentrated to a yellow oil, and purified by silica gel column chromatography using 3% methanol/methylene chloride. A yellow foam was recovered as the product (43%). MS=637 (M+H), 659 (Na+).

EXAMPLE 108

Compound 120

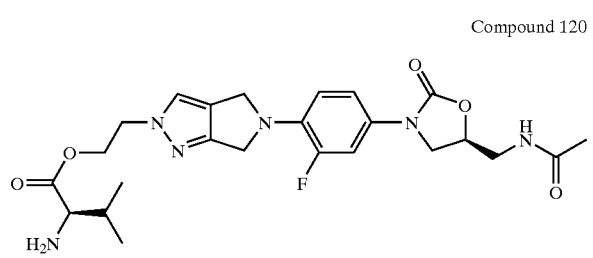

A solution of Compound 119 (0.134 g, 0.210 mmol) in MeOH (5 mL), THF (2.5 mL) and water (1 mL) was added to 0.67 mL of 0.5 N aqueous HCl and 0.014 g 10% Pd on C. The mixture was shaken under an initial pressure of 50 psi $H_2$ at RT for 18 hr. At this time, the reaction mixture was filtered through Celite, eluting the product with methanol. The filtrates were concentrated in vacuo to give an off-white foam. This product was purified by preparative reverse-phase HPLC using 0.1% AcOH as an additive. The diacetate salt was isolated as a white powder (0.060 g, 43%). MS=503 (M+H), 525 (Na+).

Compound 119

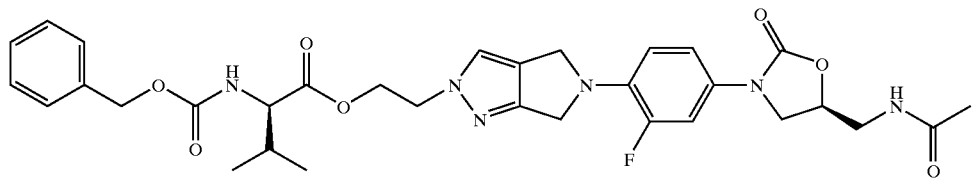

EXAMPLE 109

Compound 121

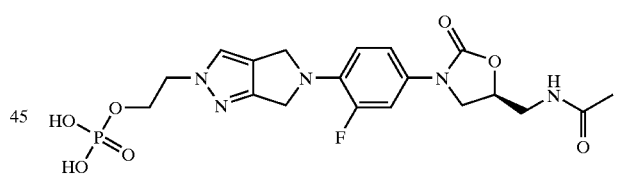

To a solution of Compound 114 in $CH_2Cl_2$ is added TFA. The reaction mixture is stirred for 30 min and the solvent is removed on a rotavap. The product is isolated by triturating with ether to give a solid. (M+H)=484.

The invention has been described in detail with particular reference to the above embodiments thereof. The above embodiments and examples are given to illustrate the scope and spirit of the present invention. These embodiments and examples will make apparent, to those skilled in the art, other embodiments and examples. These other embodiments and examples are within the contemplation of the present invention. It will be understood that variations and modifications can be effected within the spirit and scope of the invention; therefore, the instant invention should be limited only by the appended claims.

We claim:
1. A compound having the formula:
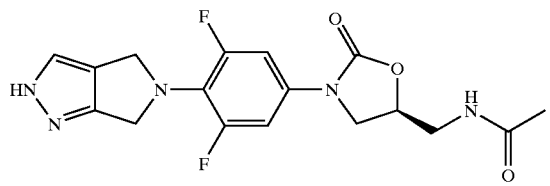
2. A compound having the formula:
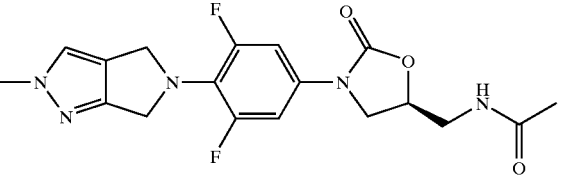
3. A compound having the formula:
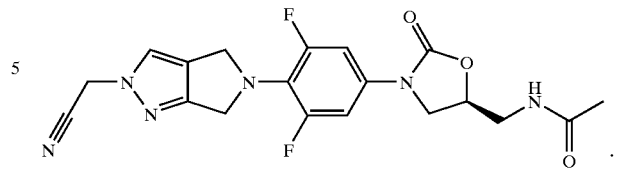
4. A compound having the formula:
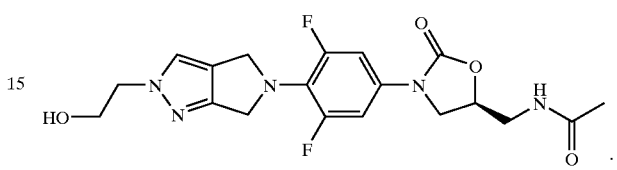
5. A compound having the formula:
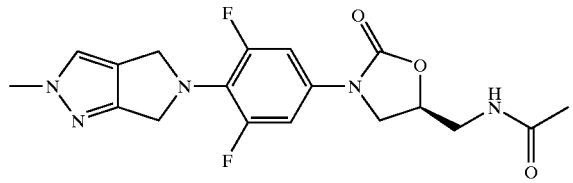
* * * * *